(12) United States Patent
Utz et al.

(10) Patent No.: US 8,524,061 B2
(45) Date of Patent: Sep. 3, 2013

(54) ON-CHIP HYBRIDIZATION COUPLED WITH ITP BASED PURIFICATION FOR FAST SEQUENCE SPECIFIC IDENTIFICATION

(75) Inventors: Paul J. Utz, Portola Valley, CA (US); Juan G. Santiago, Stanford, CA (US); Michael G. Kattah, Boston, MA (US); Alexandre Persat, Metuchen, NJ (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 170 days.

(21) Appl. No.: 13/373,773

(22) Filed: Nov. 29, 2011

(65) Prior Publication Data
US 2012/0160689 A1    Jun. 28, 2012

Related U.S. Application Data

(60) Provisional application No. 61/458,674, filed on Nov. 29, 2010.

(51) Int. Cl.
*G01N 27/447*   (2006.01)
*G01N 27/26*    (2006.01)

(52) U.S. Cl.
USPC .............................. 204/549; 204/645; 435/6.1

(58) Field of Classification Search
USPC .................................. 204/549, 645; 435/6.1
See application file for complete search history.

(56) References Cited

U.S. PATENT DOCUMENTS

| | | |
|---|---|---|
| 3,869,365 A | 3/1975 | Sunden |
| 3,948,753 A | 4/1976 | Arlinger |
| 4,897,169 A | 1/1990 | Bier et al. |
| 5,447,612 A | 9/1995 | Bier et al. |
| 5,464,515 A | 11/1995 | Bellon |
| 5,817,225 A | 10/1998 | Hinton |
| 5,939,291 A | 8/1999 | Loewy et al. |
| 6,685,813 B2 | 2/2004 | Williams et al. |
| 6,780,584 B1 | 8/2004 | Edman et al. |

(Continued)

FOREIGN PATENT DOCUMENTS

| | | |
|---|---|---|
| EP | 1742057 | 1/2007 |
| EP | 2340122 A1 | 7/2011 |

OTHER PUBLICATIONS

Persat et al., "Quantification of global microRNA abundance by selective isotachophoresis", 2010, pp. 9631-9635, Anal. Chem. v82.

(Continued)

*Primary Examiner* — J. Christopher Ball
*Assistant Examiner* — Jennifer Dieterle
(74) *Attorney, Agent, or Firm* — Lumen Patent Firm

(57) ABSTRACT

Isotachophoresis (ITP) can be employed to simultaneously focus the target and ligand of an assay into the same ITP focus zone. The target and ligand can bind to each other in the ITP focus zone, and then the resulting bound complex can be detected (e.g., by fluorescence). The sensitivity of this approach can be greatly increased by the enhanced concentration of both target and ligand that ITP provides in the focus zone. Since ITP can be performed quickly, the resulting assay is both rapid and sensitive. Markers of bacterial urinary tract infections have been experimentally detected at clinically relevant concentrations with this approach. MicroRNA sequences have also been profiled with this approach, which is clinically relevant because MicroRNA is expected to provide useful markers for disease. In one experiment, miR-122 in human kidney and liver was detected and quantified.

22 Claims, 13 Drawing Sheets

(56) References Cited

U.S. PATENT DOCUMENTS

| | | |
|---|---|---|
| 6,818,113 B2 | 11/2004 | Williams et al. |
| 6,934,836 B2 | 8/2005 | Strand et al. |
| 7,214,299 B2 | 5/2007 | Armstrong |
| 7,223,325 B2 | 5/2007 | Landers et al. |
| 7,316,771 B2 | 1/2008 | Weber |
| 7,371,533 B2 | 5/2008 | Slater et al. |
| 7,399,394 B2 | 7/2008 | Weber |
| 7,473,551 B2 | 1/2009 | Warthoe |
| 7,494,577 B2 | 2/2009 | Williams et al. |
| 7,517,442 B1 | 4/2009 | Champagne |
| 7,635,563 B2 | 12/2009 | Horvitz et al. |
| 7,951,278 B2 | 5/2011 | Santiago et al. |
| 8,017,408 B2 | 9/2011 | Meinhart et al. |
| 8,021,531 B2 | 9/2011 | Park et al. |
| 8,133,371 B2 | 3/2012 | Marziali et al. |
| 8,277,628 B2 | 10/2012 | Ronaghi et al. |
| 8,394,251 B2 | 3/2013 | Santiago et al. |
| 2004/0031683 A1 | 2/2004 | Eipel et al. |
| 2005/0121324 A1 | 6/2005 | Park et al. |
| 2005/0133370 A1 | 6/2005 | Park et al. |
| 2005/0170362 A1 | 8/2005 | Wada et al. |
| 2006/0042948 A1 | 3/2006 | Santiago et al. |
| 2006/0078998 A1 | 4/2006 | Puskas et al. |
| 2008/0000774 A1 | 1/2008 | Park et al. |
| 2008/0020386 A1 | 1/2008 | Chen et al. |
| 2008/0021674 A1 | 1/2008 | Puskas |
| 2008/0156080 A1 | 7/2008 | Balgley |
| 2008/0166770 A1 | 7/2008 | Morita et al. |
| 2009/0178929 A1 | 7/2009 | Broer et al. |
| 2010/0084271 A1* | 4/2010 | Santiago et al. ............ 204/549 |
| 2010/0116657 A1 | 5/2010 | Fiering et al. |
| 2010/0224494 A1 | 9/2010 | Chambers et al. |
| 2010/0261612 A1 | 10/2010 | Young |
| 2010/0270157 A1 | 10/2010 | Kurosawa et al. |
| 2010/0323913 A1 | 12/2010 | Young et al. |
| 2011/0024296 A1 | 2/2011 | Park et al. |
| 2011/0036718 A1 | 2/2011 | Jung et al. |
| 2011/0174624 A1 | 7/2011 | Weber |
| 2011/0220499 A1 | 9/2011 | Chambers et al. |
| 2011/0297546 A1 | 12/2011 | Schoch |
| 2012/0061242 A1 | 3/2012 | Santiago et al. |
| 2012/0152746 A1 | 6/2012 | Santiago et al. |
| 2012/0160689 A1 | 6/2012 | Utz et al. |
| 2012/0175258 A1 | 7/2012 | Mariella, Jr. |

OTHER PUBLICATIONS

Goet et al., "Micro contact based on isotachophoretic sample transport", 2009, pp. 3586-3593, Lab Chip v9.

Park et al., "Controlling data quality and reproducibility of a high-sensitivity immuniassay using isotachophoresis in a microchip", 2008, pp. 808-814, Anal. Chem. v80.

Persat et al., "Purification of nucleic acids from whole blood using isotachophoresis", 2009, pp. 9507-9511, Anal. Chem. v81.

Persat et al., "Towards an on-chip isothermal polymerase chain reaction", 2007, pp. 56-58, Proceedings MicroTAS 2007.

Berkovici et al., "Rapid detection of urinary tract infections using isotachophoresis and molecular beacons", May 5, 2011, pp. 4110-4117, Analytical Chemistry v83.

Persat et al., "MicroRNA profiling by simultaneous selective isotachophoresis and hybridization with molecular beacons", Feb 18, 2011, pp. 2310-2316, Analytical Chemistry v83.

US 7,247,224, 07/2007, Weber (withdrawn).

Gohring, et al. The scaffold/matrix attachment region binding protein hnRNP-U (SAF-A) is directly bound to chromosomal DNA in vivo: a chemical cross-linking study. Biochemistry. Jul. 8, 1997;36(27):8276-83.

Morio, et al. Quantitative analysis of trifluoroacetate in the urine and blood by isotachophoresis. Anesthesiology. Jul. 1980;53(1):56-9.

* cited by examiner

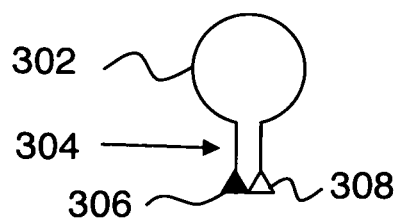
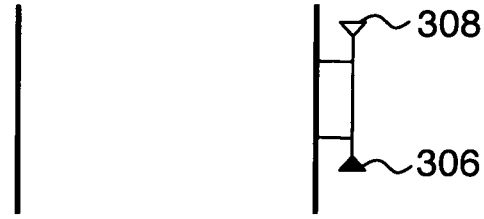
Fig. 3a  Fig. 3b  Fig. 3c
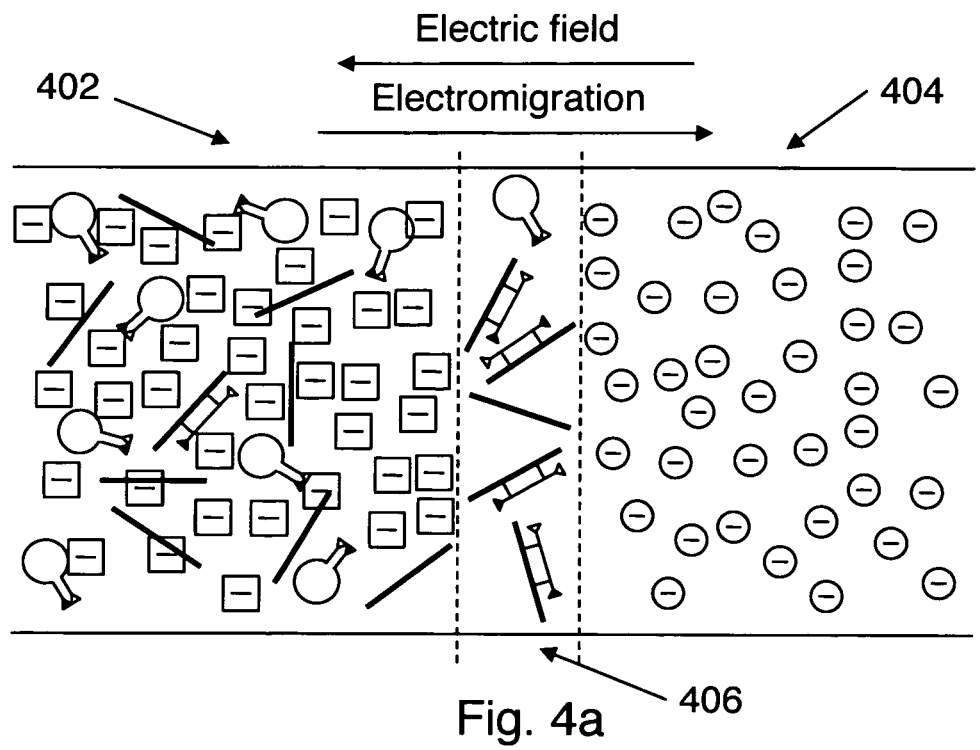
Fig. 4a
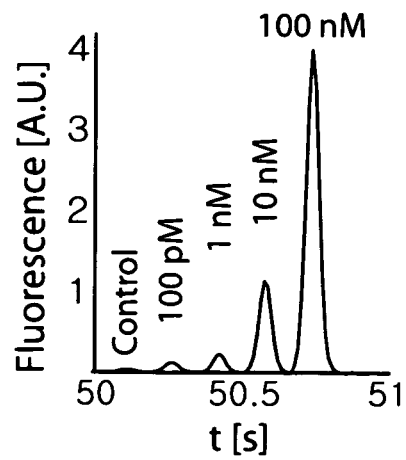
Fig. 4b

US 8,524,061 B2

ON-CHIP HYBRIDIZATION COUPLED WITH ITP BASED PURIFICATION FOR FAST SEQUENCE SPECIFIC IDENTIFICATION

CROSS REFERENCE TO RELATED APPLICATIONS

This application claims the benefit of U.S. provisional patent application 61/458,674, filed on Nov. 29, 2010, entitled "On-chip hybridization coupled with ITP based purification for fast sequence specific identification", and hereby incorporated by reference in its entirety.

GOVERNMENT SPONSORSHIP

This invention was made with Government support under contract RR025742 awarded by the National Institutes of Health. The Government has certain rights in this invention.

FIELD OF THE INVENTION

This invention relates to biological sample analysis and/or preparation via isotachophoresis (ITP).

BACKGROUND

Biological assays are of considerable and growing importance for scientific research and for medical practice. In many cases, biological assays can take an undesirably long time to perform. For example, medical tests for bacterial infections often take several days because a bacterial culture is made. Culturing can be avoided by more sensitive assay techniques, such as sequence identification via the polymerase chain reaction (PCR). However, a PCR assay is also time consuming and costly.

Accordingly, it would be an advance in the art to provide biological assays having improved performance and speed. In particular, it would be an advance in the art to detect markers for infection and/or disease at clinically relevant concentration levels in real time (i.e., <1 hour).

SUMMARY

Isotachophoresis (ITP) can be employed to simultaneously focus the target and ligand of an assay into the same ITP focus zone. The target and ligand can bind to each other in the ITP focus zone, and then the resulting bound complex can be detected (e.g., by fluorescence). The sensitivity of this approach can be greatly increased by the enhanced concentration of both target and ligand that ITP provides in the focus zone. Since ITP can be performed quickly, the resulting assay is both rapid and sensitive. Markers of bacterial urinary tract infections have been experimentally detected at clinically relevant concentrations with this approach. MicroRNA sequences have also been profiled with this approach, which is clinically relevant because MicroRNA is expected to provide useful markers for disease. In one experiment, miR-122 in human kidney and liver was detected and quantified, and the results show significantly higher level of miR-122 in liver than in kidney, as expected.

BRIEF DESCRIPTION OF THE DRAWINGS

FIGS. 3a-c show features of labeling with molecular beacons.

FIG. 4a schematically shows ITP separation in a first example of the invention (detection of infections).

FIG. 4b shows experimental results relating to the first example.

DETAILED DESCRIPTION

This description is organized into three sections. Section A provides an overview of general principles relating to the present approach. Section B relates to rapid detection of urinary tract infections (first example). Section C relates to microRNA profiling (second example).

A) General Principles

As indicated above, the present approach is based on focusing a target and a ligand to the same zone by ITP, so that bound complexes of target-ligand form in the ITP focus zone. The bound complexes can then be analyzed to provide information on the target species.

Figure 1A:
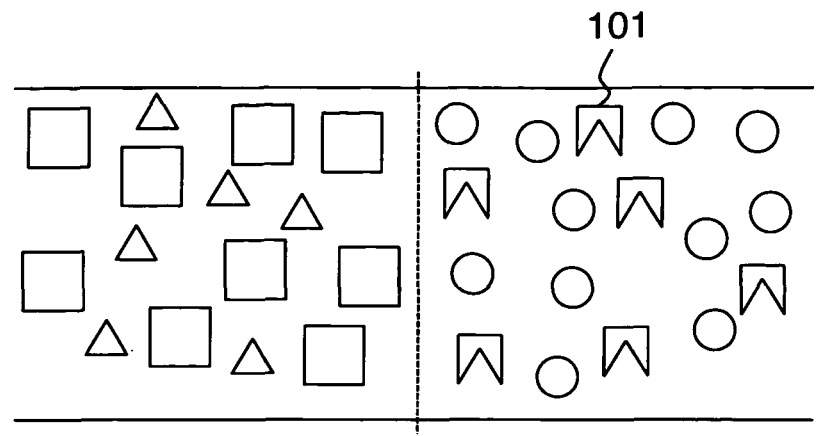
FIGS. 1a-b show an example of separation according to an embodiment of the invention.
Figure 1B:
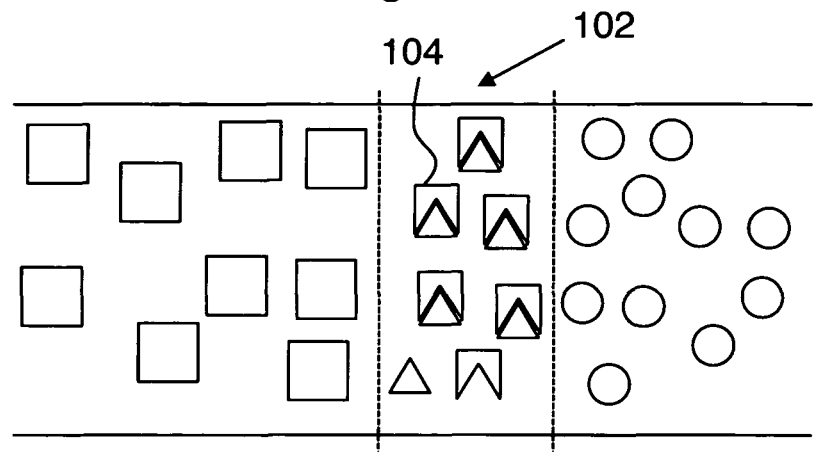

More specifically, and with reference to FIG. 1a, a sample can include a trailing ion TE (squares), a leading ion LE (circles), a target (notched shape, one of which is referenced as 101 on FIG. 1a), and a ligand (triangles). Initially, the target and ligand can be mixed with the LE and/or the TE, e.g. as shown. As ITP proceeds, both the target and ligand focus to the same ITP zone, and bind to each other to form bound complexes. The resulting configuration is shown on FIG. 1b. Here the ITP zone is referenced as 102, and one of the bound complexes is referenced as 104. The ligand and/or the target include a nucleotide sequence, thereby enabling a variety of assays that rely on specificity to nucleotide sequences. In order to obtain the desirable configuration of FIG. 1b, it is necessary to design the ITP separation such that the effective mobilities of both the target and the ligand are between the effective mobilities of the LE and TE. As a result of this double focusing, the target and ligand are both significantly concentrated, thereby making the resulting assay significantly more sensitive and specific. This improved performance is a significant advantage provided by this approach, especially since ITP assays can be performed much more quickly than other approaches, such as the polymerase chain reaction (PCR).

In some embodiments, the ligand includes a molecular beacon molecule that has a fluorescence signal that increases substantially upon hybridization. Molecular beacons are described in greater detail in the following examples. Briefly, a molecular beacon (MB) has a fluorophore at one end and a quencher at the other end. When the MB is not hybridized, it assumes a configuration where the fluorophore and quencher are in proximity to each other such that fluorescence is substantially quenched by the quencher. When the MB is hybridized, it assumed a configuration where the fluorophore and quencher are sufficiently far from each other such that fluorescence is substantially unaffected by the quencher.

Figure 1C:
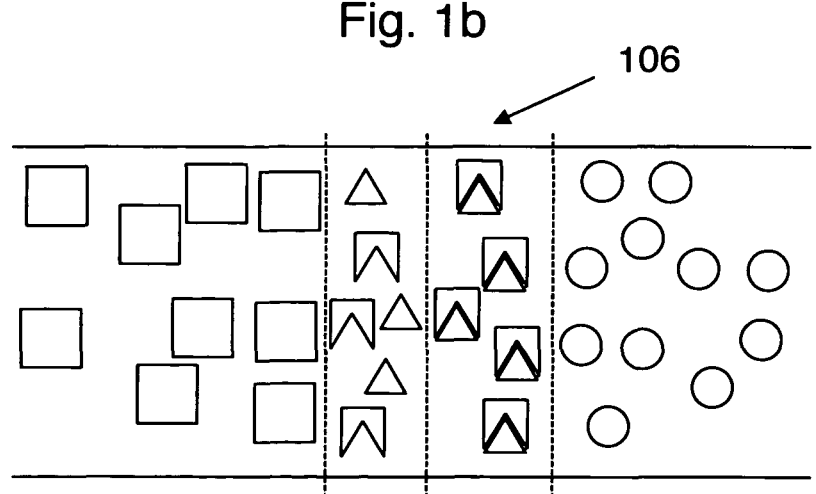
FIGS. 1c-e show separation according to some exemplary embodiments of the invention.
Figure 1D:
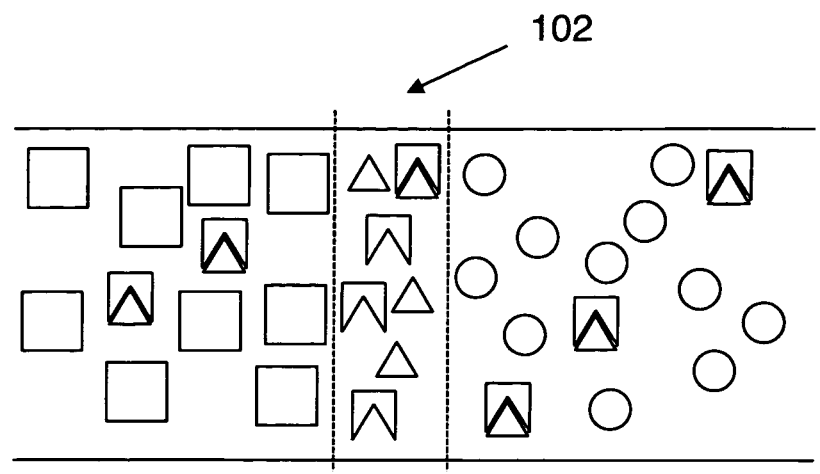

In some embodiments the effective mobility of the bound complex and the effective mobility of the ligand differ. This can have various effects. One possibility is that the bound complex remains in the ITP focus zone of the ligand and target (i.e., as shown on FIG. 1b). FIG. 1c shows an example where bound complexes focus in a second ITP zone 106 that is distinct from the first ITP zone 102 where the ligand and target focus. Another possibility is that the effective mobility of the bound complex can be such that it does not focus via ITP after formation, which may lead to a configuration as shown on FIG. 1d, where the bound complex is not focused between the TE and LE.

Once bound complexes have been formed as described above, separation of the ligand, target and/or the bound complex can be performed. This further processing can be useful for sample preparation (e.g., preparation of bound complex, which may or may not be concentrated). Any separation method can be employed for this further separation, including but not limited to: isotachophoresis, electrophoresis, and chromatography.

Figure 1E:
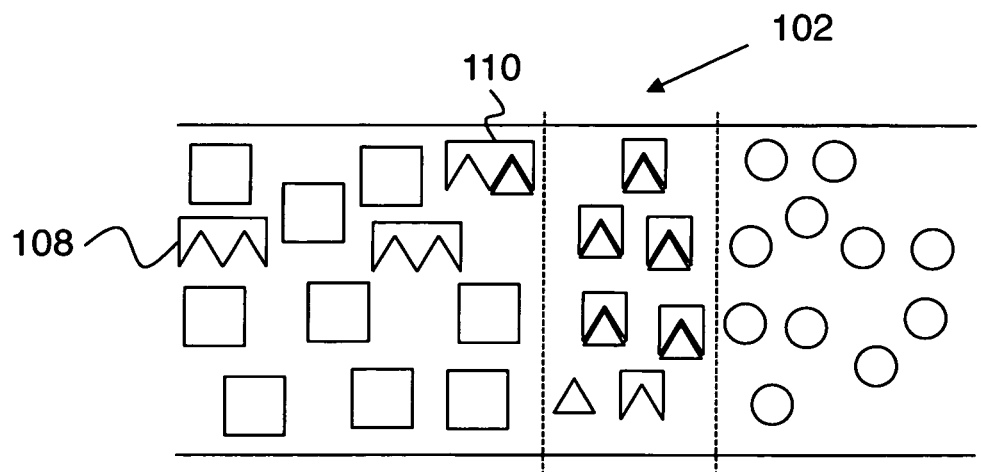

The present approach can be advantageous in situations where the sample include target(s) and target precursor(s), and the precursors are also capable of binding the ligand. FIG. 1e schematically shows an example. The target precursors (one of which is referenced as 108) can form bound complexes with the ligand. One of these precursor bound complexes is referenced as 110. In situations like this, it is preferred that the target precursor not focus in ITP zone 102 where the target focuses. As a result of this separation, signals from the target and precursor are spatially separated, thereby helping to distinguish target form precursor. Furthermore, the precursor has little chance to bind with the ligand, because the ligand concentration is low where the precursors are located (i.e., outside the ITP focus zone).

Figure 2A:
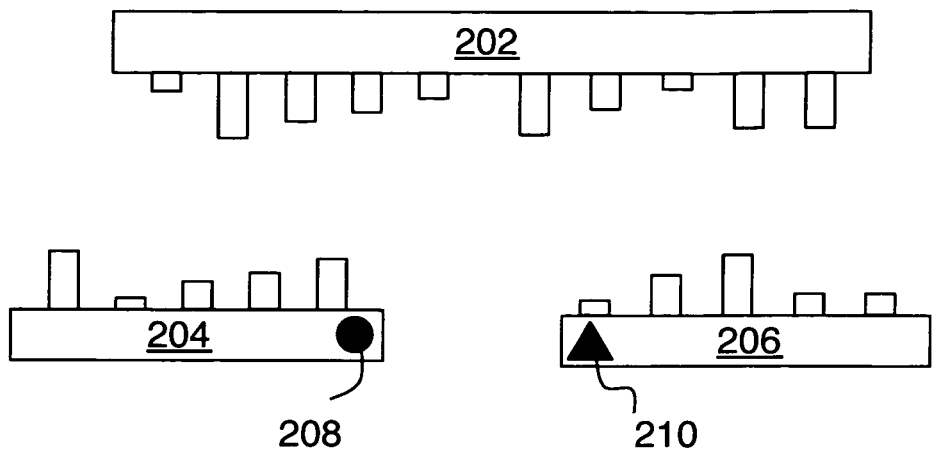
FIGS. 2a-b show an example of cooperative labeling.
Figure 2B:
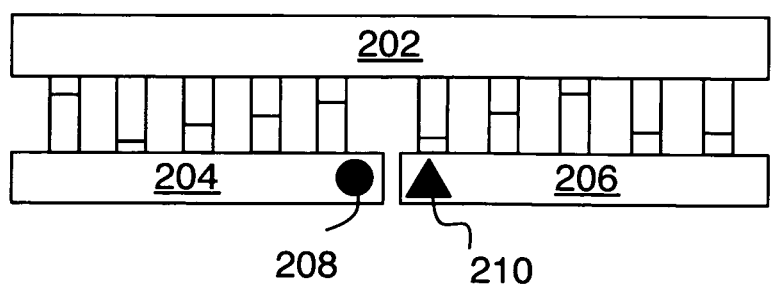

Cooperative labeling can be employed in connection with embodiments of the invention. FIGS. 2a-b show an example of cooperative labeling. Here, a target 202 is capable of binding two (or more) ligand molecules (204 and 206 in this example). FIG. 2a shows the separate molecules, and FIG. 2b shows the corresponding bound complex. In this example ligand molecule 204 includes fluorophore 208, and ligand molecule 206 includes a fluorophore 210. The cooperative labeling can be provided by Förster resonance energy transfer (FRET) where excitation of fluorophore 208 leads to emission from fluorophore 210 (or vice versa) by FRET. This process relies on spatial proximity of fluorophores 208 and 210, which occurs in bound complexes and is highly unlikely to occur for unbound ligand molecules. Thus, when bound, the two fluorophores are at adjacent ends of the ligand molecules (e.g., as shown on FIG. 2b). Equivalently, ligand molecules 204 and 206 are adjacent to each other along the target in the bound complex, fluorophore 208 on ligand molecule 204 is in proximity to ligand molecule 206 and fluorophore 210 on ligand molecule 206 is in proximity to ligand molecule 204.

Various methods of detection can be employed for the bound complexes. For example, the ligand can be labeled with a fluorescent label. Also, the ligand can include a chemical group with strong ultra-violet light absorption. Alternatively, the target can be labeled with a fluorescent label and the ligand can include a quencher that corresponds to the label on the target.

The ligand can include a nucleotide hybridization probe (which can be fluorescently labeled). Targets can include nucleic acid species, polypeptides capable of binding to a nucleic acid, and proteins capable of binding to a nucleic acid. Nucleotide hybridization probes can include nucleic acid probes and aptamers.

The target and ligand can be partially hybridized prior to performing ITP as described above. In this situation, the above described steps serve to further enhance the bound complex formation relative to the ITP initial conditions.

This approach can be used for sample analysis and/or preparation. For example, concentrated bound complex can be extracted from ITP focus zone 102 of FIG. 1b. Analysis of the bound complex can be performed in the ITP zone of the target and ligand (e.g., as in the example of FIG. 1b), or may be performed elsewhere in the ITP stack, depending on where the bound complex ends up (e.g., as in the examples of FIGS. 1c and 1d).

The present approach is applicable to any application of sample analysis and/or preparation. Biological or medical applications are of particular interest. For example, clinical screening for infection can be accomplished by obtaining a patient specimen (e.g., urine sample, blood sample etc.), and performing the above described analysis, where the ITP sample is derived from the patient specimen, and the ligand is capable of binding to a target species that is a marker for disease. Such target species that are markers for disease can include bacterial nucleotide sequences, viral RNA or DNA sequences, mitochondrial DNA sequences, micro RNA sequences, or messenger RNA sequences that encode host or pathogen proteins involved in disease, etc. The disease marker may be a nucleic acid marker used to identify one or more pathogens causing infections. This marker may be RNA or DNA and the pathogens may be bacteria, fungi, mycobacteria, prions, or viruses. Alternately, the marker may be a peptide, polypeptide, or protein associated with a disease state. The protein may be associated with a pathogen or with the body's response to the pathogen or disease process.

As indicated below, the present approach has demonstrated rapid detection (<1 hour) of infection markers at clinically relevant levels, which is a significant and surprising advance relative to the state of the art (e.g., several days for a bacterial culture).

B) Rapid Detection of Infections

B1) Introduction

Infectious diseases caused by bacterial and other infectious pathogens remain one of the most common causes of mortality worldwide. Urinary tract infection (UTI) is the second most common infection in the United States affecting all patient demographics, with approximately 8 million visits to outpatient clinics and emergency departments, and 100,000 hospitalizations each year. Overall, medical expenditures for UTI in the United States are estimated to be $3.4 billion. Similar to most other bacterial infections, diagnosis of UTI requires a centralized clinical microbiology laboratory and trained professionals to perform bacterial culture and phenotyping, which typically takes 1-3 days. A rapid, inexpensive, definitive test capable of detecting pathogens in urine would be enormously beneficial in ensuring timely treatment, in eliminating empirical treatment, and in reducing costs and burden on the health care system.

Several nucleic acid amplification techniques such as polymerase chain reaction (PCR) and real-time PCR genotyping tests have been developed for bacterial identification. Such tests have recently been implemented on microchips but require elaborate off-chip preparation including the extraction and purification of nucleic acids. Other approaches include microarray-based tests requiring pre-amplification of the target, and immunoassays typically require sequential processes such as multiple washes, incubations and the implementation of specialized chemistries for signal amplification/transduction.

PCR-based techniques are yet to replace standard bacterial culture due to their complexity, cost and need for specially trained personnel. PCR-free assays, in which the genetic content of the sample could be directly analyzed, could offer a simple yet specific diagnostic tool, while alleviating or eliminating many of the constraints associated with genetic amplification. We here present a novel assay for UTI detection in which we use isotachophoresis (ITP) to extract, focus, and hybridize bacterial-specific 16S ribosomal RNA (rRNA) with sequence-specific molecular beacons, directly from urine pellet lysate. ITP is an electrophoretic technique in which only ions with mobilities bracketed by those of a leading electrolyte (LE) and trailing electrolyte (TE) are focused to achieve both sensitivity and selectivity. ITP has earlier been applied to urine samples, primarily for measurement of small molecules. The latter studies have been typically performed on long separation capillaries using electrochemical detection, electric potentials of 10 kV or higher, and separation times on the order of tens of minutes to hours. More recently, on-chip ITP has been applied to extraction and purification of biological samples: ITP has been used for extraction of short RNA from bacterial lysate using a sieving matrix, extraction of DNA from whole blood has been performed using ITP, and ITP has been used for extraction of DNA from cultured bacteria lysate.

We have adapted a chemical lysing technique compatible with ITP, and applied ITP for focusing and detection of 16S rRNA in cell cultures and patient urine samples using molecular beacons. Bacteria cells contain on the order of 10,000 ribosomes (this value varies according to the growth stage of the bacteria), each consisting of several ribosomal subunits. These subunits, typically characterized by the Svedberg unit (indicating their sedimentation rate under centrifugation), consist of an RNA sequence bound to multiple proteins. 16S rRNA is a 1542 nucleotide long well-characterized bacterial-specific biosignature. It is commonly targeted in molecular assays, due to its high abundance (5.5% by weight) in bacterial cells.

Molecular beacons are sequence specific nucleic acid probes that fluoresce upon hybridization. Developed in the early years of quantitative PCR, molecular beacons have become ideal sequence-specific fluorescent reporters for nucleic acid amplifications assays and in vivo hybridization. The sequence specific fluorescence of MBs originates from their unique structure shown in FIG. 3a. MBs are composed of four units: (i) a nucleic acid probe sequence 302 (the loop, up to about 30 nt long) complementary to the target sequence of interest; this sequence is flanked by (ii) two, complementary self-hybridizing sequences 304 which allow conformation of the probe into a hairpin structure, (iii) a fluorophore 306 at the 5' end, and (iv) a suitable quencher 308 at the 3' end. We present a schematic of the MB hybridization reaction mechanism in FIGS. 3a-c. When the molecular beacon is free in solution, it acquires a hairpin structure (FIG. 3a) which brings 5' and 3' ends in proximity, so the quencher hampers fluorescence. In the presence of a sequence complementary to the probe (e.g., sequence of FIG. 3b), the hairpin opens and hybridizes to the target (FIG. 3c). This is thermodynamically favorable because the short stem hybrid is less stable than the longer probe-target hybrid. In this configuration, the distance between fluorophore and quencher is sufficient to enable fluorescence.

MBs have mostly been applied in conjunction with real-time PCR for the quantitative detection of bacteria, viruses, single nucleotide polymorphisms and for real-time intracellular monitoring. Since 50% of urine samples which are sent for bacterial analysis are returned with a negative result, the ability to quickly rule out an infection is of high value. We therefore focus on demonstration of our assay using a universal bacterial probe, which targets a highly conserved region of bacterial 16S rRNA.

To the best of our knowledge, this work is the first demonstration of on-chip ITP for rapid pathogen detection. This assay requires minimal sample preparation (a single centrifugation and dilution), and performs extraction, focusing, and detection of 16S rRNA in a single step, and without the use of a sieving matrix. Currently, the entire assay, from beginning of lysing to detection, can be completed in under 15 min, and is sensitive within a clinically relevant range of bacteria concentration (1E6-1E8 cfu/mL). We believe that by varying the molecular beacons probe sequence, the principles presented here could be used for other rapid diagnostics, including other pathogenic diseases.

B2) Principle of the Assay

FIG. 4a is a schematic showing simultaneous isotachophoretic extraction, focusing, hybridization (with molecular beacons), and detection of 16S ribosomal RNA bound to a molecular beacon. Hybridization of the molecular beacon to 16S rRNA causes a spatial separation of its fluorophore and quencher pair resulting in a strong and sequence-specific increase in fluorescent signal.

FIG. 4a schematically presents the principles of the assay. ITP uses a discontinuous buffer system including LE (circles) and TE (squares), which are typically chosen to have respectively higher and lower electrophoretic mobility than the analytes of interest. Both sample and molecular beacons are initially mixed with the TE. When an electric field is applied, all species with mobility higher than that of the TE electromigrate into the channel. Other species (including ones with lower mobility, neutral or positively charged) remain in or near the sample reservoir. Focusing occurs within an electric field gradient at interface between the LE and TE, as sample ions cannot overspeed the LE zone but overspeed TE ions. The resulting configuration has a ITP focus zone 406 disposed between an LE zone 404 and a TE zone 402.

We designed ITP buffers to focus 16S rRNA, molecular beacons, and their (possible) complex at the interface. Their hybridization produces a sequence-specific fluorescence signal which we use to both identify and quantify bacteria. In positive control experiments, we modeled 16S rRNA using synthetic oligonucleotides with a complementary sequence to the molecular beacon probe. The probe used in this work targets a 27 nucleotide sequence common to all bacteria, and has been validated in previous work with a large cohort of clinical samples using electrochemical detection.

FIG. 4c presents example quantitative detection of the oligonucleotides. Each curve presents the fluorescence intensity in time, as recorded by a point detector at a fixed location in the channel (curves are shifted in time for convenient visualization). 100 pM of molecular beacons and varying concentrations of targets were mixed in the trailing electrolyte reservoir. The total migration (and hybridization) time from the on-chip reservoir to the detector was less than a minute.

As the target concentration increased, a higher fraction of the beacons were hybridized and fluorescence signal (the area under the peak) increased. For the highest target concentration presented (100 nM), the fluorescence signal was approximately 100-fold higher than the control case (with no target oligonucleotides). The lowest concentration of synthetic targets we detected was 100 pM, corresponding to a fluorescent signal approximately 3-fold higher than the control case.

B3) Theory

In this section we present theory useful in quantitative analysis of the beacons signal. First, we define the enhancement ratio, a normalized figure of merit for quantifying the increase in signal due to beacon-target hybridization. We use this definition to explore the sensitivity and limit of detection of the assay and highlight the key parameters useful in optimizing the assay.

The fluorescence signal of a mixture of beacons and target, F, can be expressed as, $$F = \alpha \frac{c_{BT}}{c_B^{tot}} + \beta \frac{c_{B,closed}}{c_B^{tot}} + \gamma \frac{c_{B,open}}{c_B^{tot}}, \quad (1)$$

where $c_{BT}$, $c_{B,closed}$, and $c_{B,open}$ are the concentration of the hybridized beacons, closed stem beacons, and open stem (random coil) beacons respectively. $c_B^{tot}$ is the total concentration of beacons, and $\alpha$, $\beta$, $\gamma$ are the conversion factors for fluorescent intensity associated with each respective state.

It is convenient to measure the signal with respect to the signal of a control case, $F_0$, which contains the same concentration of beacons $c_B^{tot}$, but no targets $$F_0 = \beta \frac{c_{B,closed}^0}{c_B^{tot}} + \gamma \frac{c_{B,open}^0}{c_B^{tot}}. \quad (2)$$

Here $c_{B,closed}^0$ and $c_{B,open}^0$ are the concentrations of the two beacon states in the absence of any target. We define the ratio of signal to control signal as the enhancement ratio, given by $$\varepsilon = \frac{\alpha c_{BT} + \beta c_{B,closed} + \gamma c_{B,open}}{\beta c_{B,closed}^0 + \gamma c_{B,open}^0}. \quad (3)$$

We use this enhancement ratio as an internally-normalized figure of merit which is less sensitive than the absolute fluorescence values to experimental conditions such as illumination intensity, degree of photobleaching, and exposure time. While the hybridization reaction likely does not reach full equilibrium within the time scales of our experiments, it is instructive to perform equilibrium analyses to explore the limits of detection of the assay.

We now assume chemical equilibrium of the beacon and target reaction to explore maximum signal values and some trends also relevant to unsteady problems. Assuming equilibrium, the concentrations of all species can be related to the equilibrium and mass conservation equations as follows:

$$\text{(i) } K_{12} = \frac{c_{B,closed} c_T}{c_{BT}} \quad (4)$$

$$\text{(ii) } K_{23} = \frac{c_{B,open}}{c_{B,closed}}$$

$$\text{(iii) } c_{BT} + c_{B,closed} + c_{B,open} = c_B^{tot}$$

$$\text{(iv) } c_{BT} + c_T = c_T^{tot},$$

where $c_T^{tot}$ is the total concentration of the target. Applying relations (4), and denoting $\beta^* = \beta + \gamma K_{23}$, we have $$\varepsilon = \frac{\alpha c_{BT} + \beta^* c_{B,closed}}{\beta^* c_{B,closed}^0}. \quad (5)$$

To allow rapid quantification and sensitivity to target, we here explore the regime in which $c_T^{tot} \ll c_B^{tot}$, and assume $K_{12} \ll c_T^{tot}$. The latter regime holds for most beacons and concentrations higher than 1 fM, as calculated based on published values for the Gibbs free energy. In this regime, $c_{BT} \approx c_T^{tot}$ and, from (4iii), $c_{B,closed} = (c_B^{tot} - c_T^{tot})/(1+K_{23})$. Assuming $K_{23} \ll 1$ (which holds for typical molecular beacons stems), the equilibrium enhancement ratio is thus $$\varepsilon \approx \frac{\alpha c_T^{tot} + \beta^*(c_B^{tot} - c_T^{tot})}{\beta^* c_B^{tot}} = 1 + \left(\frac{\alpha}{\beta^*} - 1\right)\frac{c_T^{tot}}{c_B^{tot}} \text{ for } c_T^{tot} \leq c_B^{tot} \quad (6)$$

For the beacon quencher pair used in this work, we estimate $\alpha/\beta^*$ is approximately 80 (based on measurements at high target concentrations). The dynamic range of the assay is thus between $\epsilon=1$ (no target) and $\epsilon=80$ (for $c_T^{tot} \approx c_B^{tot}$). As we shall see below, this result, although assuming equilibrium, agrees with our experimental observations which showed a detectable range over two orders of magnitude of bacteria concentration (1E6 to 1E8 cfu/ml).

In this work, we use a point detector to record the fluorescence signal at the ITP interface, as it electromigrates through the detection point. We therefore find it useful to relate this temporal signal to the dynamics of the assay. Denoting the signal distribution in the channel (i.e. in space) as f(x), and the integration window of the detector as w(t), the signal in time is given by the convolution of the two, $$s(t) = \int_{-\infty}^{\infty} f(x_d - V_{ITP}\tau) w(t-\tau) d\tau, \quad (7)$$

where $x_d$ denotes the location of the detector, and $V_{ITP}$ is the velocity of the ITP plug (assumed here for simplicity as constant).

Since peak signal values are sensitive to noise and sampling rate, it is convenient to quantify the intensity of the signal by the total fluorescence, i.e. area under the signal curve, $$A = \int_{-\infty}^{\infty} s(t)\,dt.$$

The enhancement ratio $\epsilon$ can then be computed as $\epsilon = A/A_0$, where $A_0$ corresponds to area under the signal curve for a negative control. By change of variable, $\eta = V_{ITP}\tau$, and noting that the term $f(x_d - \eta)$ is independent of t, we can express $$A = \frac{1}{V_{ITP}} \int_{-\infty}^{\infty} f(x_d - \eta) \left[ \int_{-\infty}^{\infty} w\!\left(t - \frac{\eta}{V_{ITP}}\right) dt \right] d\eta. \quad (8)$$

For any value of $\eta$, and any finite integration window, the term in brackets is constant, and the area under the curve is given by $$A = \frac{C_1}{V_{ITP}} \int_{-\infty}^{\infty} f(x_d - \eta)\,d\eta. \quad (9)$$

The integral over the signal f is also constant, and therefore the total fluorescence integral A is inversely proportional to the migration velocity $V_{ITP}$. In a spatial image of the ITP interface taken after a fixed time from beginning of the experiment (e.g. using a CCD), the effect of the interface velocity on total fluorescence is minimal, since a fixed pre-determined exposure time is used. In contrast, a point detector (e.g. a PMT) continuously records the light intensity. Total fluorescence therefore depends directly on the velocity of ITP, i.e. the duration of time in which the detector is exposed to the fluorescent peak. For a quantitative ITP assay with a point detector, it is therefore important that the migration velocity of plug over the detection point be repeatable across experiments. In practice, this requirement translates to repeatable suppression of electroosmotic flow (EOF) and sufficient dilution of the sample to avoid sample-specific variations in buffer conductivities (which in turn alter the electric field and hence ITP velocity). In the current experiments, we used real-time current monitoring as an indicator of ITP velocity, and this is further discussed in the results section.

B4) Experimental Section

B4a) Experimental Setup

Briefly, we used a 0.9 numerical aperture water-immersion objective to collect the light emitted by the molecular beacons within the microfluidic chip. A 400 μm pinhole was placed at the image plane, allowing collection of light from within the 12 μm deep channel, while rejecting out-of-focus light. The light was refocused onto a PMT for detection. Excitation is performed using a variable-power laser diode coupled into the illumination port of the microscope using a multimode optical fiber. The beam is expanded and collimated before being focused onto the channel using the same objective used for light collection. A CCD camera is used for alignment of the laser and microchannel prior to each experiment.

More specifically, we mounted a microfluidic chip on the stage of IX70 inverted epifluorescent microscope (Olympus, Hauppauge, N.Y.). Constant voltage was applied using a sourcemeter (2410, Keithley Instruments, Cleveland, Ohio). We used a 642 nm variable-power laser diode (Stradus-642, Vortran Laser Technologies, CA) as the excitation light source. The light from the laser was coupled to the illumination port of the microscope using a multimode optical fiber (M31L05) with a fiber coupler (FiberPort PAF-X-7-A) on the laser end, and a beam collimator and expander (F230FC-A) on the microscope end, all from Thorlabs (Newton, N.J.). The laser beam passed through the excitation filter of a Cy5 filter-cube (Cy5-4040A, Semrock, Rochester, N.Y.), and was focused onto the chip using a water immersion objective (LUMPlanFL 60×, NA=0.9, Olympus, Hauppauge, N.Y.). Light was collected by the same objective passed through the emission filter of the filter cube. We constructed a point-confocal setup by placing a 400 μm pinhole at the focal plane of the microscope's side-port to reject out of plane light. Light was then focused onto a photomultiplier tube (PMT) module (H6780-20, Hamamatsu Photonics, Japan) using a 1 in biconvex lens with a focal length of 50 mm (LB1471-A, Thorlabs Newton, N.J.). The assembly of the PMT, lens, and pinhole was mounted on three micro stages, to provide three degrees of freedom in aligning the pinhole with the laser spot. The PMT signal was digitized using a data acquisition unit (C8908, Hamamatsu Photonics, Japan) and communicated via RS232 to a PC. The PMT was powered using 5V DC from a stable power source (E3631A, Agilent, Santa Clara, Calif.) and operated at a sampling rate of 100 Hz. We used in-house MATLAB® codes (R2007b, Mathworks, Natick, Mass.) to simultaneously control and record the data from both the PMT and the sourcemeter.

B4b) Cell Cultures and Clinical Samples

With approval from Stanford University Institutional Review Board, bacterial isolates and clinical urine samples were obtained from informed, qualified study participants at risk for UTI. We prepared pellets from both *E. coli* cultures and human urine by centrifuging 1 mL of sample at 10,000 g for 2 min, and then discarding the supernatant. The pellets were kept frozen at −80° C.

B4c) Buffers, Lysing Reagents, and Probes

ITP: For all experiments, the leading electrolyte (LE) was composed of 250 mM HCl and 500 mM bistris, 5 mM $MgCl_2$, and 1% 1.3 MDa poly(vinylpyrrolidone) (PVP). The trailing electrolyte (TE) was composed of 50 mM tricine and 100 mM bistris. We used a high ionic strength LE to maximize the focusing rate of species. $Mg^{2+}$ ions were used as a second counter ion (in addition to bistris) to promote rapid hybridization of the beacons and target rRNA at the ITP interface. PVP was used in the LE for suppression of electroosmotic flow (EOF). The TE concentration was empirically determined to provide sufficient buffering and repeatability over a range of samples (additional details in the results section), while also promoting focusing rate. Tricine, bistris, and $MgCl_2$ were obtained from Sigma-Aldrich (St. Louis, Mo.). PVP was obtained from ACROS Organics (Thermo Fisher Scientific, N.J.).

Lysis:

Lysis was composed of two steps using two sets of reagents. Lysis reagent I was composed of 10 mM Tricine, 10 mM BisTris, 2 mM EDTA (GIBCO Invitrogen, Carlsbad, Calif.), 0.1% Triton-X, and 5 mg/mL lysozyme (both from Sigma-Aldrich, St. Louis, Mo.). Lysis reagent II was composed purely of 400 mM NaOH (Sigma-Aldrich, St. Louis, Mo.).

Beacons:

The beacons solution contained 50 mM tricine, 100 mM bistris, 5 mM $MgCl_2$, and 1 nM of molecular beacons (IDT, Coralville, Iowa). We chose a 27-mer probe sequence which was shown in the art to detect a wide range of urinary pathogens. We added 6 base-pairs to either side of the probe to form the molecular beacon stem. The 5' terminus was labeled with Cy5, and the 3' terminus was labeled with Black Hole Quencher 2 (BHQ2). For the control experiment, we designed a molecular beacon with an inverted probe sequence. In this beacon we have also swapped cytosine for guanine at the tip of the stems, to preserve the same level of quenching by the nucleotide closest to the 5' dye (cytosine is a weaker quencher than guanine). The two beacons are thus very similar in their thermodynamic properties, but the inverted probe cannot hybridize to the 16S rRNA target sequence.

All solutions were prepared in UltraPure DNase/RNase free deionized (DI) water (GIBCO Invitrogen, Carlsbad, Calif.). Buffer stock solutions were prepared in 80 mL glass bottles (VWR, Radnor, Pa.) and kept at room temperature. 50 mg/mL of lysozyme were prepared from powder and kept at 4° C. for no more than a week. All solutions were freshly prepared at the beginning of each set of experiments. Lysis reagent I was kept on ice when not in use.

B4d) Assay Description and Microchip Implementation

Figure 5A:
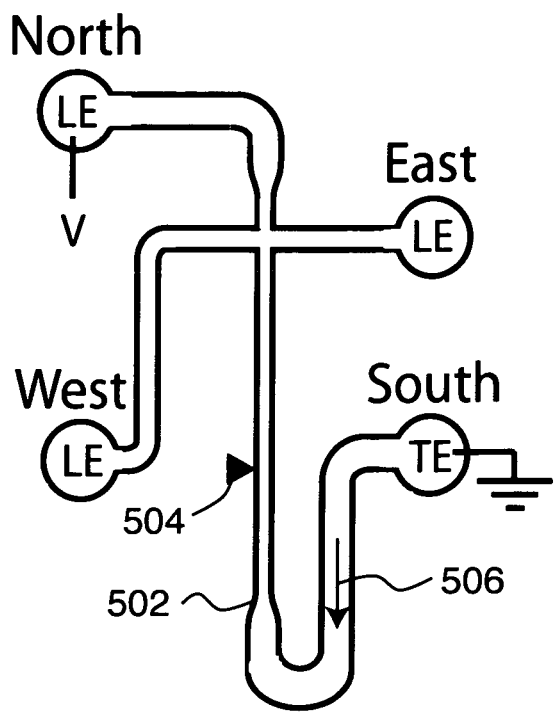
FIG. 5a shows the ITP arrangement for the first example.
Figure 5B:
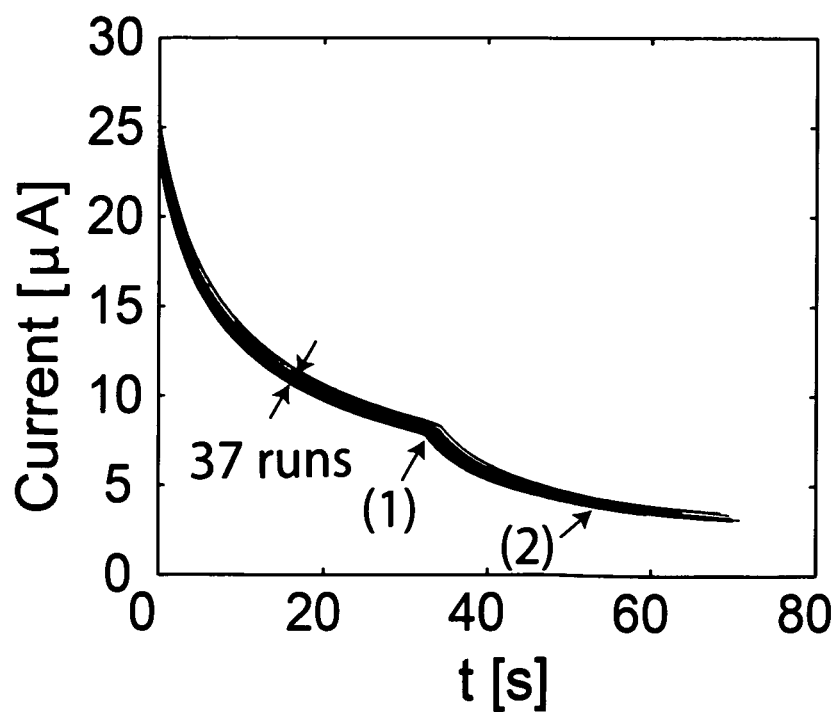
FIG. 5b shows the results of repeated runs in the first example.
Figure 5C:
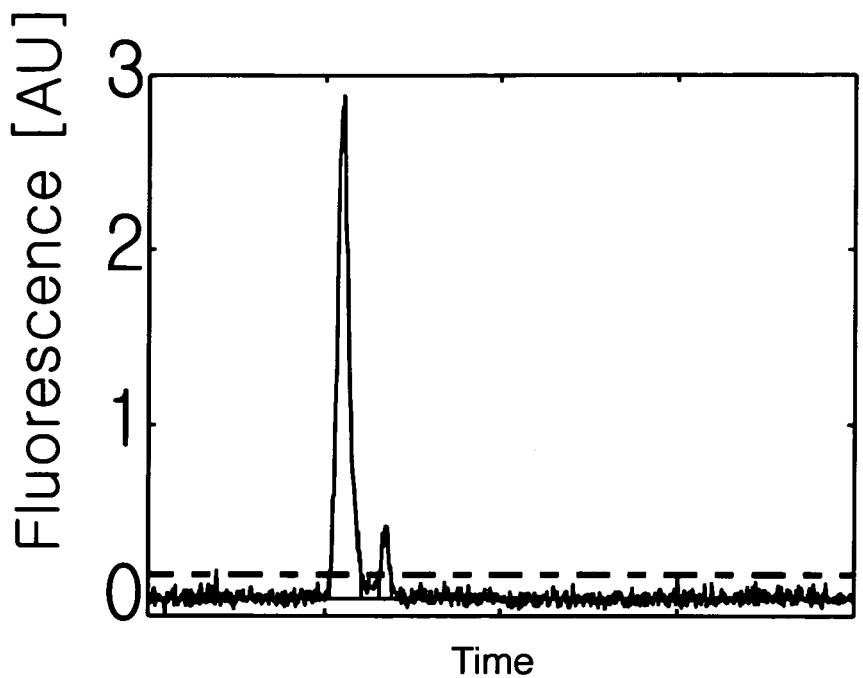
FIG. 5c shows an experimental fluorescence electropherogram of a bacterial sample in the first example.
Figure 5D:
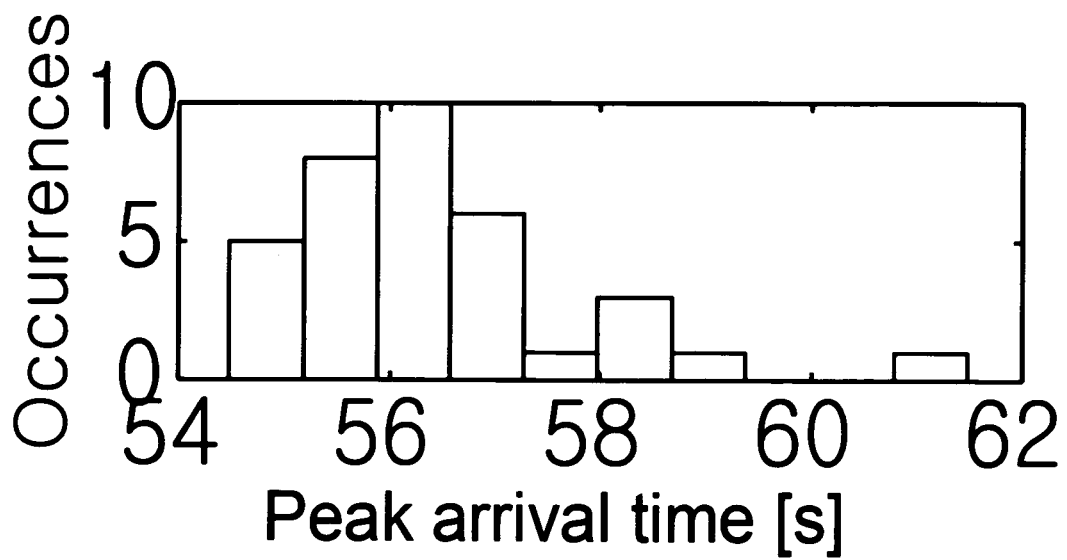
FIG. 5d is a histogram of experimental peak arrival time distribution for the runs of FIG. 5b.

FIGS. 5a-d show the microfluidic chip and experiments to establish analyte quantitation. FIG. 5a is a schematic of the microfluidic chip showing the direction of electromigration (arrow 506), the area where channel width decreases (502), and location of detector (504). FIG. 5b shows current measurements. Current was measured in real-time for all experiments. Current monitoring is important for interpretation of fluorescence signal integrals and allows detection of unwanted effects such as clogging of the channel or significant variations in initial conditions. Sample lysing (and dilution) were optimized for repeatability. Shown are overlayed time traces of 37 runs for sample concentrations of 1E6 to 1E8 cfu/ml and negative control samples. FIG. 5c shows a typical fluorescent signal with a bacterial sample. We integrate the signal to estimate the total amount of focused sample. We determine signal baseline using the Auto-Leveling Baseline Correction method (which is known in the art) and then integrate the data in regions where values are 5 standard deviations above the standard deviation of the baseline noise. Integration values are computed with respect to the mean background noise (i.e., only the parts of the peaks above the solid line on FIG. 5c contribute to the integral). FIG. 5d is a histogram showing the distribution of peak arrival time for the 37 runs presented in FIG. 5b. The standard deviation of arrival times (at (1)) is less than 5% of the mean.

For experiments involving cell cultures or patient urine, we resuspended the pellet in 80 µL of DI water, and actuated the pipette several times to homogenize the solution. We added 10 µL of lysis reagent I, and incubated for 5 min at room temperature. We then added 10 µL of lysis reagent II and actuated the pipette until the solution became clear and transparent. For experiments using bacterial cultures, we diluted the sample down from an initial concentration of 1E8 cfu/mL. We separated 10 µL of this lysate and mixed it with 90 µL of beacons solution. Since we initially resuspended the cells in 100 µL and then diluted 10 fold, the final target concentration is equal to its initial concentration in the 1 ml urine sample. We incubated the sample off-chip for 5 min at 60° C. prior to introducing to chip (see discussion of FIG. 5b).

For chip loading, we pipetted 2 µL of the sample/beacons mixture into the South reservoir of the chip containing 20 µL of TE. For the positive control experiments in which a synthetic target was used (FIG. 1c), we skipped the lysing and incubation steps, and directly introduced 2 µL of 1 nM beacons, and 2 µL of varying concentration of synthetic target into the TE (South) reservoir. In all cases, we used commercially available microfluidic chips made of borosilicate (NS-95) from Caliper Life Sciences (Mountain View, Calif.). The channel is isotropically etched to a depth of 12 µm and includes a 54 µm wide section which constricts into a 34 µm wide section. The total length of the channel is 34.6 mm, with the initial (wide) section 11.5 mm in length. The chip layout is depicted schematically in FIG. 5a.

At the beginning of each set of runs, we cleaned the channel by flowing 200 mM NaOH for 5 min, and then rinsed the channel with DI for 2 min. For each experiment, we filled the North, East and South reservoirs with 20 µL of LE and applied vacuum to the West reservoir (connected to the longest channel) until all channels were filled. We then rinsed the West reservoir with DI water, and filled it with 20 µL of TE and 2 µL of the sample/beacons mixture. We use a semi-infinite sample injection (where sample is mixed with the TE) as it allows increasing the total amount of focused sample by continuously focusing new sample at the interface. This is in contrast to finite injection, where the amount of sample is limited to the injection volume. We then applied 1.1 kV between the East and West reservoirs and detected at a distance of 19 mm from the West reservoir. Note we do not use or need the "cross" channel intersection of the chip, and the experiment can be realized with a single, straight channel.

B5) Results and Discussion

B5a) Repeatability of ITP Velocity and Temporal Fluorescence Signals

The analysis presented in the theory section suggests that repeatability of ITP velocity is important for quantitative measurements using a point detector. To monitor ITP velocity for each experiment, we used a sourcemeter to apply constant voltage while measuring current. Initially, the channel was filled entirely with LE. As the ITP interface electromigrated, the lower conductivity TE replaced the LE. This resulted in an increase of the overall resistance of the channel and a gradual decrease in current. FIG. 5b presents 37 overlaid curves of current versus time for experiments performed in the same day, and using both bacterial sample concentrations ranging from 1E6 to 1E8 cfu/ml and negative control samples. The expected, abrupt change in slope of the curve near 35 s (labeled (1)) corresponds to the time when the ITP interface moves into the narrow region of the channel (c.f. FIG. 5a). FIG. 5d presents the distribution of the peak's arrival time at the detector for these 37 experiments. The standard deviation of arrival time at the detector is less than 3% of the mean.

Application of constant current is often preferred over constant voltage for electrophoretic assays, as it allows maintaining constant electric fields, and its results are simpler to interpret and analyze. However, application of constant current has a significant disadvantage: for a given maximum power supply voltage, the maximum allowable current must be set according to maximum resistance in channel. This maximum resistance is only achieved at the end of the run. Since the ITP velocity is directly proportional to the current, this results in significantly longer assay times. For example, in FIG. 5b we show that, under constant voltage, current decreases from approximately 25 µA at t=0, to 2.5 µA at t=60 s. Performing the same assay under constant current conditions (and using the same power source) conditions would require to set the current at 2.5 µA throughout, resulting in approximately 7 fold increase in assay time. The results in FIGS. 5a-d indicate assay time can be minimized using constant voltage, without compromising for repeatability.

Using equation (9), we can propagate this uncertainty to the enhancement ratio, for which the standard deviation is also 3%. FIG. 5c presents a typical raw signal recorded by the PMT. We observed in several experiments double peaks such as the one presented in the figure (with one peak having a significantly lower intensity and lower area then the other). We hypothesize that some 16S rRNA degradation takes place, resulting in RNA fragments. Although theoretically all species should overlap under peak mode ITP, a previous study showed that carbonic acid (naturally present in the buffers) often results in separation of species at the interface. To account for this, and since peak intensities are highly sensitive to sampling rate and dispersion, we use 'total fluorescence' as the integral of the signal (area under the curve). As discussed in the theory section, we then describe the signal enhancement factor as $\epsilon = A/A_0$, where A is the area under the signal peak, and $A_o$ is the value for the control case. To integrate the signal peak, we first determined the baseline using the GIFTS method. The signal magnitude is the value above this baseline. We then integrate the signal only in regions where the signal is 5 standard deviations above the baseline.

B5b) Effect of Off-Chip Incubation on on-Chip Assay

We analyzed the effect of initial off-chip incubation times at 60° C. to complement our assay's subsequent, on-chip, ITP-aided incubation.

Figure 6:
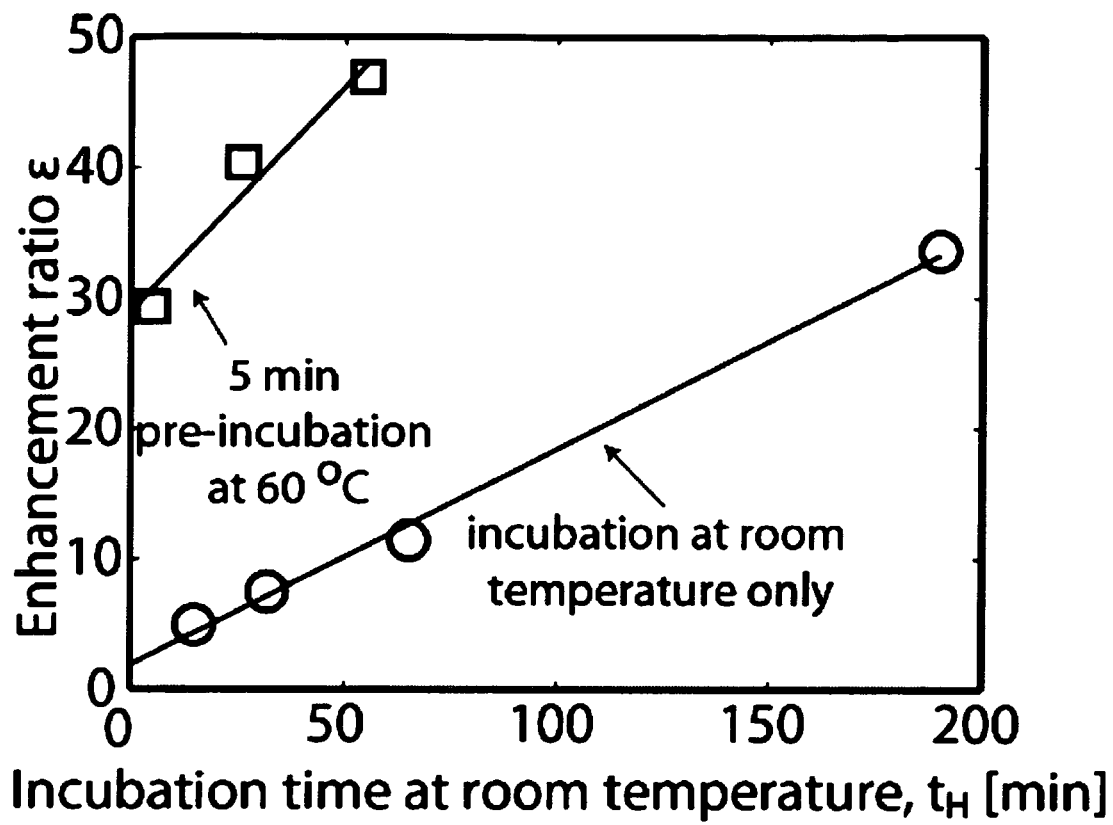
FIG. 6 shows enhancement ratio as a function of incubation time for the first example.

FIG. 6 shows assay enhancement ratio as a function of initial off-chip incubation time, $t_H$, using a bacterial culture sample. Shown are measured, post-ITP enhancement ratios as a function of off-chip incubation time, $t_H$. We tested two incubation schemes: (1) incubation at room temperature only, and (2) initial 5 min incubation at 60° C. (approximately 20° C. below the melting temperature of the probe), followed by continued incubation at room temperature. Testing the sample immediately after the 5 min incubation at 60° C. resulted in an enhancement ratio equivalent to more than 2 h of incubation at room temperature. Clearly, there is a tradeoff between the sensitivity of the assay, and the total time to complete the assay. For this work, we chose to limit the hybridization time to 5 min at 60° C. (and thereafter kept the sample on ice to minimize further hybridization). This procedure enabled detection over a range of clinically relevant bacterial concentration while keeping the total assay time under 15 min.

B5c) Detection of E. coli from Cell Cultures and Patient Urine Samples

Figure 7A:
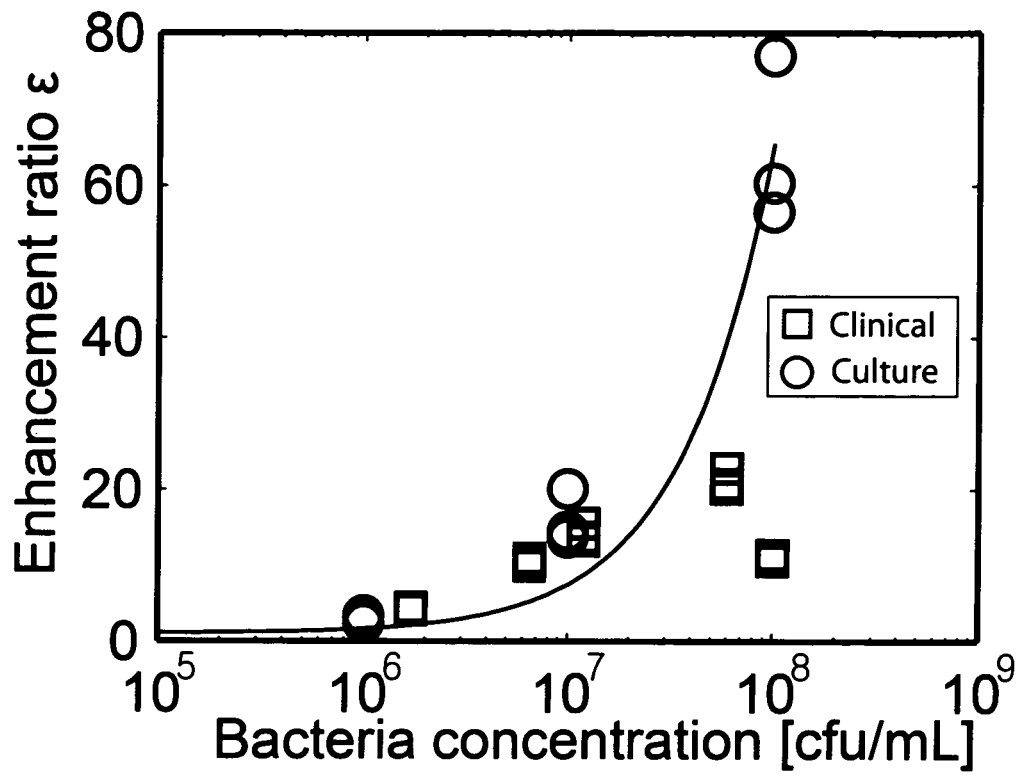
FIG. 7a shows measured enhancement ratio for both cultured samples and urine samples at clinically relevant bacterial concentrations.
Figure 7B:
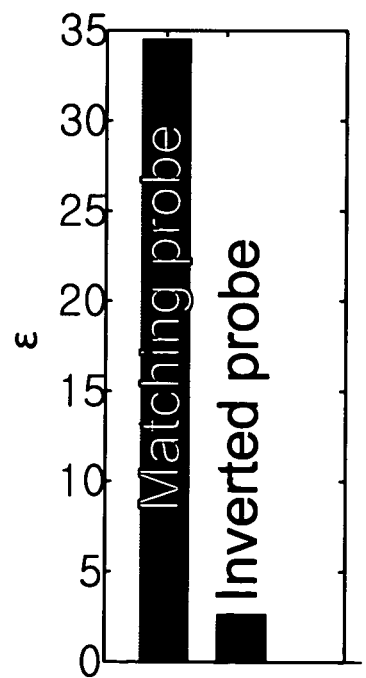
FIG. 7b demonstrates the specificity of the results of FIG. 7a by comparison with a probe having a reversed sequence.

FIGS. 7a-b show quantitative detection of E. coli 16S rRNA sequence from bacterial cultures, and bacterial detection in patient urine samples. The solid line is presented to aid visualization, and corresponds to a best linear regression fit on bacteria cultures results. 16S rRNA was extracted and focused with molecular beacons using ITP, and detected on chip. FIG. 7a shown measured enhancement ratio for cultured bacteria samples (circles) and urine samples (squares) at clinically relevant bacterial concentrations. The lysing procedure described above was used for all samples, and followed by incubation with molecular beacons for 5 min at 60° C. For each sample, the bacteria concentration was determined separately by cell plating, and is given in cfu/ml units. The limit of detection is approximately 1E6 cfu/mL, with an enhancement ratio of ~3. We checked the specificity of the probe by performing the assay with a molecular beacon having an inverted probe sequence (from 3' to 5'). While some non-specific hybridization was observed, the enhancement ratio using the inverted probe is significantly lower, as seen on FIG. 7b.

More specifically, FIG. 7a presents measured enhancement ratio versus bacteria concentration for patient-derived bacterial isolates grown in culture media, as well as for infected human urine samples. As bacteria concentration increases, a larger fraction of the molecular beacons is hybridized and the fluorescent signal and enhancement ratio increase. The enhancement ratios obtained for the clinical urine samples were overall in good agreement with the values obtained for bacteria cultures, except for the sample having a concentration of 1E8 cfu/mL. The pellet for this sample was larger, indicative of a large number of white blood cells, and consistent with the setting of a significant infection. After the standard lysis step of 5 min, there remained visible cellular aggregates suggesting that lysis was incomplete for this particularly turbid clinical sample. For consistency with other runs, we did not lengthen the lysis time and tested the sample using the same time line as described in experimental setup section. This issue of white blood cells content and its effect on signal merits further study.

Given the current choice of molecular beacon concentrations, the total assay time was approximately 15 min, and was sensitive in the clinically relevant range of (1E6-1E8 cfu/mL). The enhancement ratio for 1E6 cfu/ml was approximately 3. For a concentration of 1E5 cfu/ml (data not presented) the signal intensity was indistinguishable from the negative control case, with an enhancement ratio of approximately 1. This result is consistent with the analysis we presented in the theory section, predicting sensitivity across two orders of magnitude of sample concentration. While it may possible to improve sensitivity by reducing the level of dilution, we found this adversely affects assay repeatability. We hypothesize that this is due to the effect of higher concentrations of acids in the lysate affecting the conditions in the reservoir. We believe some of these acids overspeed the TE and create additional ITP zones between the LE and TE.

While detection of a nucleic acid sequence does not necessarily indicate viable bacteria, (if, for example, the genetic content is preserved after cell death), previous studies on electrochemical detection of 16S rRNA showed that all cases of 16S rRNA detection were confirmed by the ability to culture the bacteria by plating, which is indicative of viable bacteria. Conversely, all the samples that were sensor negative were also culture negative. Thus we conclude that the majority of 16S rRNA that we are able to detect is derived from viable bacteria. We hypothesize that RNA of dead cells may quickly degrade in urine (e.g. via RNAse), thus significantly reducing or eliminating the signal associated with their 16S rRNA content.

We also performed several control runs to ensure that the fluorescence signal was the result of probe-target hybridization. Before each set of experiments we performed ITP using the TE and LE buffers alone, and prepared new buffers from stock solution and/or replaced the microfluidic chip if contamination was observed. Between experiments using sample, we routinely performed a control run (with beacons, but without sample) to establish the baseline signal. Further, we performed experiments with cell lysate and no beacons and found it contributes negligibly to enhancement ratio. Lastly, we tested a patient-derived bacterial isolate using an inverted molecular beacon (FIG. 7b). Some increase in fluorescence was observed, likely due to non-specific binding with other regions of the rRNA. The enhancement ratio was approximately 15 fold lower than with the correct beacon.

B6) Conclusions

We demonstrated and characterized a new assay for rapid detection of UTI using ITP and molecular beacons. We use on-chip ITP to selectively focus 16S rRNA and molecular beacons directly from bacterial lysate. We perform detection of the focused hybridized complex using a point detector.

We presented detection of E. coli in bacteria cultures as well as in patient urine samples in the clinically relevant range 1E6-1E8 cfu/mL. For bacterial cultures we further presented quantification in this range. Since central clinical microbiology laboratories, including our institution, do not provide quantitative measure of concentration above 1E5 cfu/ml, we routinely perform quantitative plating and have found that vast majority of our UTI patients have bacterial concentrations of 1E6 cfu/ml or greater. Our assay therefore covers an important range of the UTI samples that are seen clinically. However, further improvements to sensitivity are required in order to encompass the entire clinically relevant range of roughly 1E5-1E8 cfu/mL. Lower molecular beacons concentrations may result in improved enhancement ratios at low bacteria concentrations (see equation (6)), but would require significantly longer hybridization times, and perhaps loss of quantitation at higher concentrations (since nearly all beacons would be hybridized above a certain target concentration). We hypothesize the most promising method of achieving high sensitivity while maintaining a short assay time is to improve hybridization rate. This may be possible by, for example, further optimization of probe sequence, stem sequence, and chemistry of fluorophore/quencher pair (i.e., improving $\alpha/\beta^*$ in equation (6)). Alternatively, this could be achieved by saturating the sample with a high concentration of beacons in the reservoir (to increase hybridization rate), and using highly specific ITP to selectively focus only the hybridized product (excluding free beacons, to avoid a high negative control signal).

In the current assay our initial samples were pellets obtained from urine sample by centrifugation. In order to achieve an automated analysis system any centrifugation steps ideally should be eliminated. Improvement of assay sensitivity may also enable detection of bacteria directly from urine with little or no off-chip sample preparation (all other steps in the assay are dilutions and mixing, functions which can presumably be implemented on chip). We demonstrated the assay using a universal prove targeting a highly conserved region of bacterial 16S rRNA. This type of test could be highly beneficial in quickly ruling out bacterial infections. We believe that by changing the molecular beacons probe sequence, the principles presented here can be directly used for detection of bacteria-specific sequences, as well as for the design of a variety of other rapid diagnostics or detection methods for pathogenic diseases.

C) Micro-RNA Profiling

C1) Introduction

MicroRNAs (miRNA) are small (~22 nucleotides), non-coding RNA molecules that regulate gene expression. Sequence specific binding of miRNAs to target messenger RNA transcripts induces gene silencing, via the formation of the RNA-induced silencing complex (RISC). miRNAs play an important role in gene regulation, both in normal pathology and disease, and therefore constitutes a marker for diverse cellular processes. In particular, profiling miRNA is potentially a powerful diagnostics and monitoring tool for cancer. Novel and improved techniques for the isolation, detection and quantification of miRNAs are currently essential to unravel the functions and mode of actions of these small molecules whose analysis by traditional techniques is still limited.

The most popular and well-established miRNA profiling methods are adapted from traditional nucleic acid analysis techniques. These include northern blot, microarrays, sequencing and reverse-transcription PCR (RT-PCR). Microarrays and sequencing platforms have high throughput but require significant instrumentation, amount of sample (about 5 µg of total RNA), are time consuming and require pre-amplification which yields significant sequence bias. RT-PCR has high dynamic range and is sensitive but has low throughput and is less specific than standard PCR. Lastly, northern blot has moderate sensitivity and allows for length discrimination of sequences, but remains time consuming and requires large amounts of sample (often >1 µg of total RNA). Northern blotting entails gel electrophoresis for separation of total RNA with subsequent transfer to a nitrocellulose membrane, followed by hybridization with a radioactively labeled probe visualized with a scintillation counter. We here adopt a different hybridization strategy which leverages isotachophoresis (ITP) and hybridization with molecular beacons (MBs) for the profiling of miRNA. Our assay is a single, amplification-free process which simultaneously purifies, preconcentrates, actively mixes, hybridizes, and produces an optical signal whose intensity increases with the initial target sample concentration.

Isotachophoresis and molecular beacons are described above. In this section, we combine selective ITP extraction and purification with MB hybridization for the sequence specific detection of miRNA. We use a multi-stage ITP injection strategy to accomplish sensitive, selective and specific detection. This multi-stage process achieves high sensitivity in an initial step, high selectivity in a second step, and conditions optimal for sensitive optical detection and hybridization in a third step. We first summarize and discuss experimental conditions of the multi stage ITP hybridization assay. Then we demonstrate hybridization and show selectivity and specificity of the assay using synthetic miRNAs. We finally apply the ITP hybridization to a biologically relevant case by detecting and quantifying a specific miRNA in human liver.

Figure 8A:
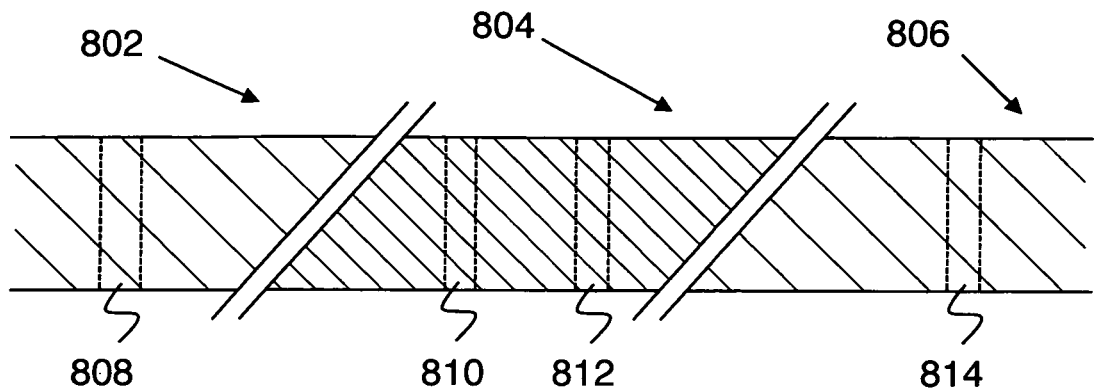
FIG. 8a schematically shows a three-stage ITP procedure relating to a second example of the invention (microRNA profiling).
Figure 8B:
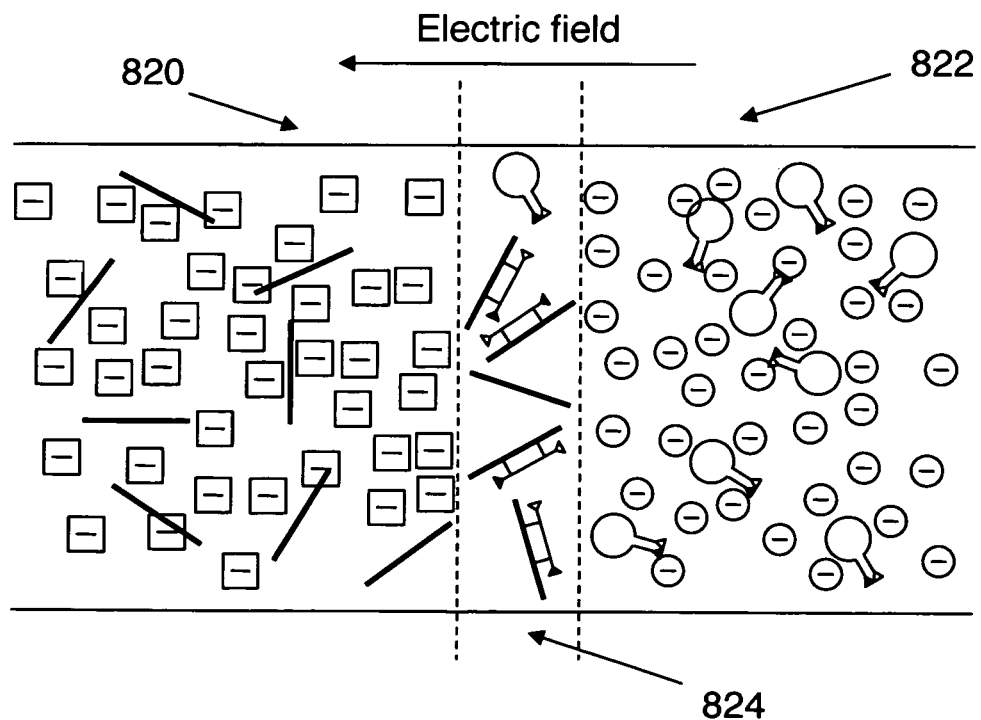
FIG. 8b schematically shows ITP separation in the second example.

FIGS. 8a-b give a schematic representation of components of the ITP hybridization assay. In FIG. 8a, we show a schematic of the three-stage ITP strategy used for purification and hybridization. We initially set up three contiguous zones of LE mixes with varying concentrations of polymer, denaturant, leading ion and magnesium chloride. The first zone LE1 (802) allows for strong preconcentration of small RNA into zone 808. The second zone LE2 (804) has higher polymer concentration (shown by increased density of hatching) to selectively focus miRNA. E.g., miRNA can focus in zone 812, and longer RNA can focus in a distinct zone 810. The third zone LE3 (806) has reduced denaturing conditions to allow for specific hybridization in zone 814 and increased quantum yield of fluorophore. The schematic in FIG. 8b demonstrates how MB can be integrated in ITP focusing. Targets (miRNA in this work) are initially in the TE zone (820) and MB in all three LE zones (822). In the frame of reference of the ITP interface, both MB and target electromigrate toward the interface between TE and LE ions. Probe and target hybridize, preconcentrate and mix in the same zone, and hybridization generates a sequence-specific fluorescence signal in the focused zone. Here the molecular beacons function as described above.

C2) Description of the Assay

We leverage the selectivity of ITP focusing to perform hybridization solely on the RNA length range of interest. Here, we selectively focus mature miRNA (18 to 24 nt) and reject all RNA molecules longer than 60 nt from the ITP zone. We therefore avoid bias from hybridization of long RNAs that contain identical or similar sequences, in particular we exclude the 70 nt long miRNA precursors pre-miRNA. This selectivity combined with the simultaneous hybridization is in some ways similar to the process of northern blotting, which requires multiple successive steps including electrophoresis and hybridization to achieve detection. In contrast to northern blotting, ITP here provides simultaneous preconcentration and active mixing of target and probe prior to and during detection.

We use a multi-zone ITP process which yields both specificity and sensitivity in the initial miRNA purification process. We created three initial contiguous LE zones arranged in series along the separation channel. Initial LE zones had distinct initial concentrations of (the same) leading ion, polymer sieving matrix, or denaturant. As ITP proceeds, the nucleic acid sample trails leading ions as these ions migrate through the successive, stationary zones of denaturant and sieving matrix (which have zero electrophoretic mobility). Here, we combine highly selective purification and preconcentration with a novel hybridization strategy. We use three successive zones to preconcentrate small RNA, select miRNA and hybridize and detect a specific target with MBs in the ITP zone.

Figure 9:
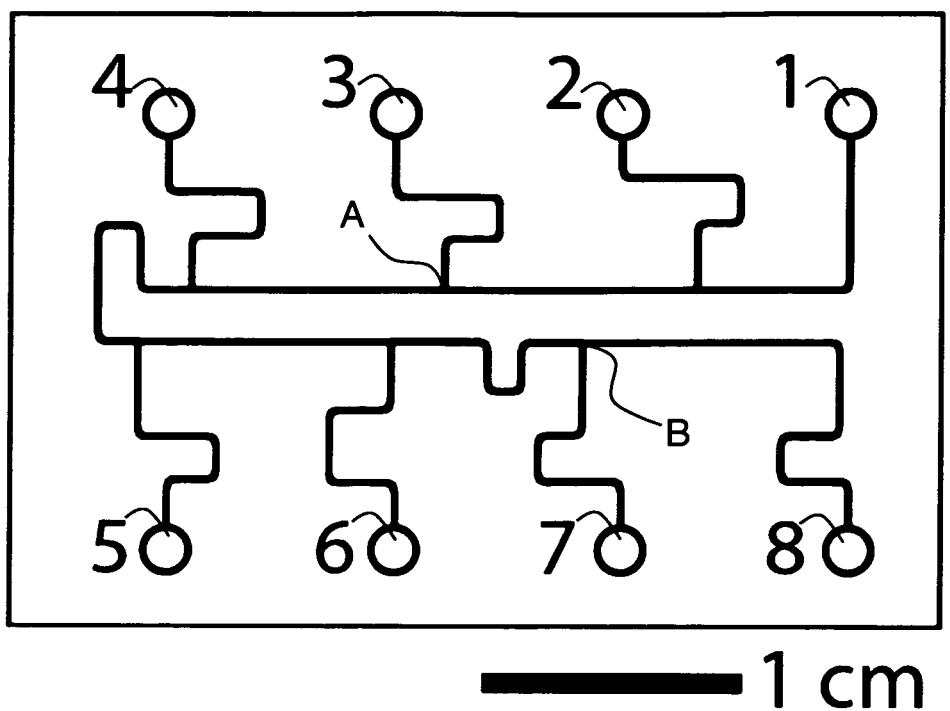
FIG. 9 shows the ITP arrangement for the second example.

The sample is mixed in the TE which includes 5 mM MOPS, 5 mM Tris and 92.5% v/v formamide. TE and sample are loaded into the sample reservoir 1 of FIG. 9. In the first zone LE1, we use a low (0.5% w/v PVP) sieving matrix polymer concentration and 7 M urea. The mobility of miRNA increases with decreasing polymer concentration, so LE1 yields a strong flux of RNA to the ITP interface, but molecules longer than (mature) miRNA molecules are also focused. Also, the slightly larger concentration of leading ions in LE1 (50 mM) augments ITP preconcentration dynamics. The second zone LE2 has large polymer concentration (3% w/v PVP), which globally decreases mobility of RNA. This defocuses longer RNA (they fall behind and out of the ITP focus zone) while leaving miRNA and MB focused, at the cost of locally retarding focusing dynamics. As discussed below, the cut off length is below 60 nt, so that miRNAs can focus, but pre-miRNAs cannot focus. Finally, LE3 has low denaturing conditions (2 M urea, lower polymer concentration of 0.5% w/v), and optimized magnesium chloride concentration (2 mM $Mg^{2+}$). These conditions enable fast hybridization, and optimize fluorescence signals as miRNAs specifically bind to MBs.

We show a detailed view of the final ITP hybridization step (occurring in LE3 zone) in FIG. 8b. Initially, MB probes targeting the miRNA of interest are dissolved in the three LEs, and total RNA (which includes miRNA) is dissolved in the TE. Leading and trailing ions are selected so that their mobilities allow for simultaneous and co-located focusing of miRNA, MB probe, and the miRNA-probe hybrid. (The latter ITP format which focuses multiple analytes into a common, sharp zone is called peak mode ITP.) Under this condition, miRNA and MB and the hybrid simultaneously focus at the interface between TE and LE. In the laboratory frame, miRNA overspeed TE ions and other RNA, and migrate toward the ITP zone. At the same time, the ITP zone overtakes and focuses MBs initially in the LE, so target and probe are actively preconcentrated and driven into ITP zone. In this focused zone, and under optimized conditions, miRNA hybridizes to the probe sequence of the MB, disrupting their hairpin structure and yielding a sequence-specific increase in fluorescence intensity within this ITP zone. This way, the focused zone acts as a reactor volume defined by its axial width and the cross sectional area of the microchannel. In our 44 μm wide, 12 μm deep channel, we estimate the volume of the ITP reaction zone to be on the order of 10 pL, given our observed ~10 μm wide ITP interfaces. This is a significantly smaller reaction volume compared to existing microfluidic reactors, which are at least on the order of few nanoliters. The strong preconcentration dynamics (we estimate order $10^3$ to $10^4$ fold increase of reactants in our conditions) yield improved kinetics and sensitivity.

C3) Materials and Methods

C3a) Chemicals and Reagents.

Leading electrolytes contain DNase- and RNase-free Tris hydrochloride buffer (pH=8.0, Invitrogen, Carlsbad, Calif.), polyvinylpyrrolidone (PVP, M.W.=1,000,000, Polysciences Inc., Warrington, Pa.), urea (EMD biosciences, Gibbstown, N.J.) and magnesium chloride (EMD biosciences, Gibbstown, N.J.). Concentrations in LE1, LE2 and LE3 are respectively 50, 20 and 20 mM of Tris hydrochloride; 0.5% w/v, 3% w/v and 0.5% w/v of PVP; 7, 7, and 2 M of urea; 0, 2 and 2 mM of magnesium chloride. The TE is a solution of 5 mM Tris (Sigma-Aldrich, Saint Louis, Mo.) and 5 mM MOPS (Sigma-Aldrich) in 92.5% v/v formamide (UltraPure, Invitrogen). All solutions were prepared with DNase- and RNase-free deionized water (Gibco, Carlsbad, Calif.).

We purchased HPLC-purified molecular beacons and synthetic miRNA from Integrated DNA Technologies (Coralville, Iowa). We used (DNA) molecular beacons, 5'-labeled with TYE 665 fluorescent dye (excitation at 645 nm and emission at 665 nm) and 3'-labeled with Iowa Black RQ quencher (peak absorbance at 656 nm). The precursor mir-26a was synthesized and PAGE-purified by Dharmacon (Lafayette, Colo.). Total RNA from normal human liver and kidney were obtained from Ambion (FirstChoice human total RNA, Austin, Tex.). Before each experiment, we dissolved the sample (total or synthetic RNA) to the specified concentration in 50 μL of TE, placed in a water bath at 70° C. for 5 min and finally on ice until running the ITP hybridization experiment. Separately, we dissolved the MB in 500 μL of each LE.

For molecular beacons, TYE 665 is a fluorophore (with spectrum similar to Cy5) and Iowa Black RQ (IBRQ) is the quencher. miRNAs and precursor are ribonucleic acids while molecular beacons are deoxyribonucleic acids.

C3b) ITP Protocol.

We here describe the injection protocol to perform the three stage ITP hybridization. We performed all experiments in an off-the-shelf borosilicate glass microfluidic chip (model NS260, Caliper LS, Mountain View, Calif.) whose design is shown on FIG. 2. The microchannels are 12 μm deep and 44 μm wide. Before each experiment, we fill the microchannels with LE1, LE2 and LE3 according the sequence described in Table 2. The multiple T-junctions of the chip of FIG. 9 enable generation of the initial serial LE zones by vacuum filling. Initially we precondition the chip by successively flushing channels with 200 mM sodium hydroxide (5 min), deionized (DI) water (1 min), 100 mM hydrochloric acid (5 min), and again DI water (1 min). We then deliver LE1 to reservoirs 1, 2 and 3; LE2 to reservoirs 4, 5 and 6; and LE3 to 7 and 8. We subsequently apply vacuum to reservoirs 3 and 7 for 5 min. These preliminary steps help reducing electroosmotic flow in the borosilicate chip for subsequent experiments.

Before each experiment, all reservoirs are rinsed with DI water. We then deliver LEs to the reservoirs as described above and in Table 1, and apply vacuum to 3 and 7 for 2 min. Vacuum at 3 generates the interface between LE1 and LE2 at the intersection A (see FIG. 9) and vacuum at 7 creates an interface between LE2 and LE3 at the intersection B. After loading, we release both vacuum connections, rinse reservoir 1 with DI water, and deliver the mixture of TE and sample. We generate an electric field in the separation channel by applying a 3 kV voltage difference between reservoir 8 and 1 using a high voltage power supply (Labsmith, Livermore, Calif.).

This activates ITP focusing and migration of miRNA and MBs through the three serial zones. We eventually stop voltage after the ITP interface has passed the detector which monitors fluorescence in the LE3 zone.

TABLE 1

Summary of the injection protocol

| | Reservoir | | | | | | | |
|---|---|---|---|---|---|---|---|---|
| | 1 | 2 | 3 | 4 | 5 | 6 | 7 | 8 |
| Step 1 | LE1, 5 µl | LE1, 5 µl | LE1, 5 µl | LE2, 5 µl | LE2, 5 µl | LE2, 5 µl | LE3, 5 µl | LE3, 10 µl |
| Step 2 | | | Vacuum 2 min | | | | Vacuum 2 min | |
| Step 3 | Empty, rinse, add 10 µl TE + sample | | | | | | | |
| Step 4 | GND | | | | | | | +3 kV |

We acquired data with an inverted epifluorescence microscope (Eclipse TE200, Nikon, Japan) equipped with a laser diode illumination (642 nm, Stradus 642, Vortran, Sacramento, Calif.). Light was filtered using a standard Cy5 cube (exciter/emitter 630/695 nm, model XF110-2, Omega Optical, Brattleboro, Vt.) and focused though a 60× water immersion objective (N.A.=1.0, Fluor, Nikon, Japan). To reduce noise from out of focus light sources, we built a custom confocal assembly by placing a 150 µm pinhole (mounted precision pinhole, Edmund Optics, Barrington, N.J.) at the image focal plane. We measured fluorescence intensity using a photomultiplier tube (PMT, model H7422-40, Hamamatsu Photonics, Japan) with voltage set to 900 V. We converted the PMT signal using an amplifier/converter unit (C7319, Hamamatsu, Japan), and filtered it with a simple low pass RC circuit (RC=1.2 ms). We acquired the resulting voltage signal with a DAQ card (NI USB-6211, National Instruments, Austin, Tex.) controlled with Matlab® (The Mathworks, Natick, Mass.). We performed all measurements at 250 kS/s data rate and applied a 4,000 points moving average to the signal for analysis. We processed the voltage trace by fitting a Gaussian function to the ITP peak. We then calculated fluorescence intensity by integrating the raw data under the fit over three standard deviations. Uncertainty bars determined from N=4 samples per condition and represent 95% confidence on the mean, calculated assuming a Student t-distribution.

C4) Results and Discussion

C4a) Initial Demonstration Using Synthetic miRNA.

Figure 10A:
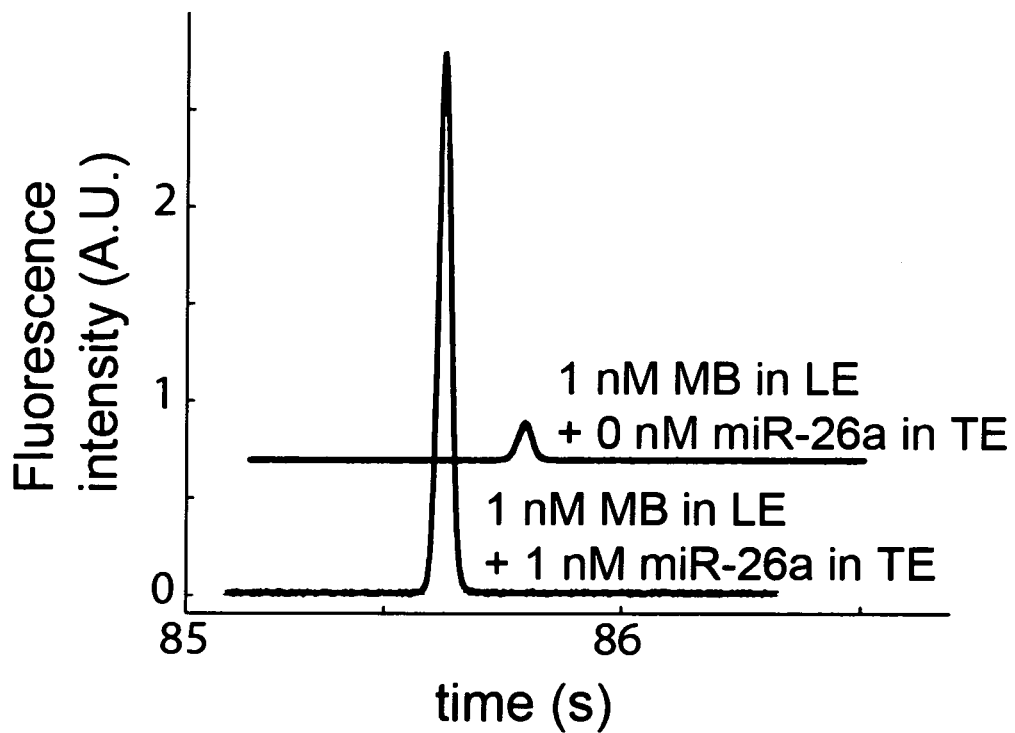
FIGS. 10a-b show ITP hybridization assay results relating to the second example.
Figure 10B:
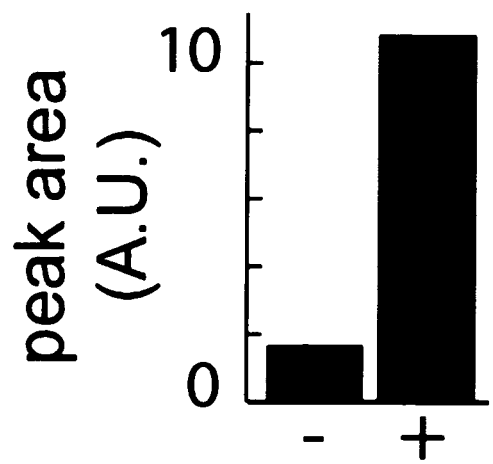

We present an example, typical ITP hybridization assay in FIG. 3. We show two isotachopherograms acquired 8 mm into the LE3 zone. In both experiments, the LE contains 1 nM of MB targeting miR-26a. The upper trace (control trace) corresponds to a negative control experiment where the TE contains no RNA. This trace exhibits a peak which we attribute to imperfect quenching of the focused MB. The lower trace (sample trace) shows the result of ITP-hybridization where we added 1 nM of miR-26a target to the TE. The ITP peak has significantly greater amplitude compared to the negative control. This demonstrates successful combination of ITP and MB based hybridization for the detection of miRNA. We report the area of each peak in FIG. 10b. The peak area of this experiment with 1 nM target in the TE (+) is more than 6 times larger than the area of the negative control (−). The control trace is displaced +0.5 s and +0.7 A.U. on the plot for clarity of presentation.

For an ITP hybridization experiment with a peak area A, we define the relative fluorescence enhancement f as:

$$f = \frac{A}{A_{nc}} - 1, \tag{10}$$

where $A_{nc}$ is the peak area of the negative control, i.e. an experiment with equal MB concentration but a blank TE. In the case presented in FIGS. 10a-b, f is approximately 5.5. f theoretically varies between zero (when $A=A_{nc}$) and a saturation value where all focused MB are open. The latter occurs when the number of target copies in the focused zone is much larger than the number of MBs.

Efficiency and speed of hybridization depend on several parameters including temperature, ion concentration, and target sequence. Here, hybridization is simultaneous and coupled with the ITP dynamics which preconcentrate beacons and target into the ITP zone. Thus, the hybridization dynamics are also coupled to ITP chemistry and conditions. The dynamics of f therefore depend on at least MB sequence and concentration, choice of fluorophore/quencher pair, temperature, ionic strength, magnesium concentration, ion mobilities (particularly TE ion mobility), applied voltage, and denaturant concentration. Here, we optimized the miRNA hybridization process empirically. Briefly, we first performed a set of control hybridization experiments off-chip using a series of beacon and target concentrations in LE and TE buffers. We quantified fluorescence signals and our signal factor f for these mixtures using a Nanodrop 3300 fluorospectrometer (data not shown). In this calibration, we also varied denaturant and magnesium concentrations and chose concentrations which maximized fluorescence enhancement for the ITP hybridization. We then tested and fine tuned these chemistries in a series of ITP experiments.

Figure 11:
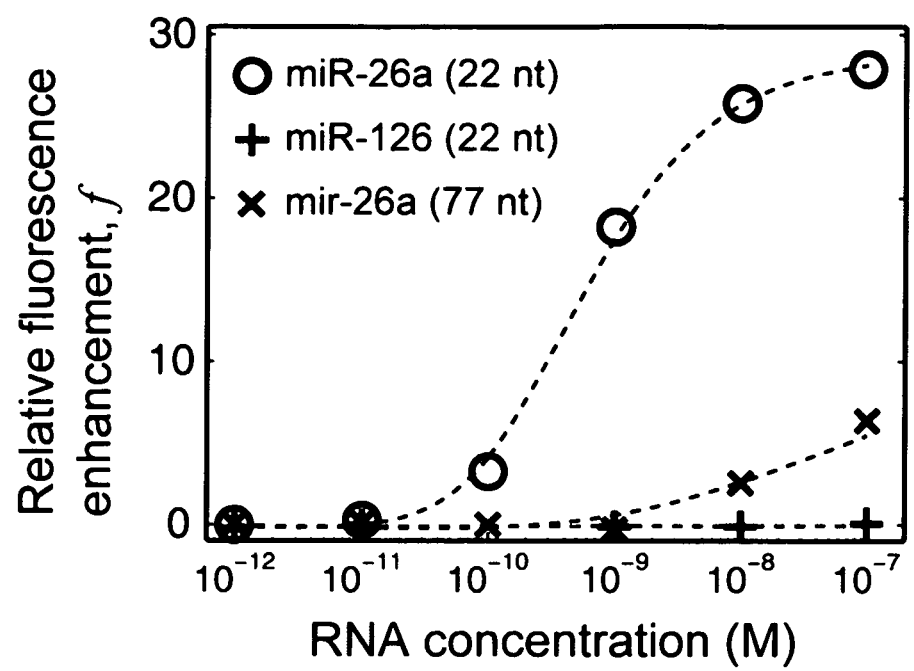
FIG. 11 provides experimental sensitivity and specificity results relating to the second example.

The fluorescence enhancement of MBs increases with target concentration. In peak mode ITP, the amount of focused sample is a linear function of sample concentration in the TE. Consequently, in the ITP hybridization assay, f increases with target concentration in the TE. We performed titration experiments to illustrate the effect of sample concentration on fluorescence enhancement. In FIG. 11, we report fluorescence enhancements for ITP hybridization at 100 pM MB with miR-26a concentrations ranging from 1 pM to 100 nM in the TE (circles).

We performed ITP hybridization with MBs targeting miR-26a and where the TE contains miR-26a (circles), miR-126 (plus) or mir-26a (cross) at concentrations ranging from 1 pM to 100 nM. We here report relative fluorescence enhancement f as defined in the text. To aid in data visualization, we fitted the data with spline functions (dashed lines). Titration with miR-26a shows the signal generated from hybridization of the perfectly matching target. Fluorescence enhancement remains small at low concentration (below 10 pM) and significantly increases at 100 pM and above. f plateaus over about 10 nM, where nearly all focused MBs are open. We also verified potential unspecific hybridization by titrating with miR-126 (whose sequence is distinct from miR-26a), and observed that fluorescence enhancement remained approximately null at all concentrations. This confirms the specificity of MB hybridization in the ITP zone. Titration with the precursor mir-26a sample shows only slow increase of fluorescence with concentration above 10 nM, since the longer molecules are filtered out by the ITP process. This shows that ITP in the LE2 zone excludes miRNA precursors from the focused zone, and allows for selective hybridization on miRNA.

At low target concentration, here 1 to 10 pM, the fluorescence enhancement remains negligible. f significantly increases above 100 pM. The most sensitive increase occurs between 100 pM and 1 nM. Above 10 nM, f varies only slightly and seems to reach a plateau value, indicating saturation of MBs. The maximum value of f in this titration experiment is approximately 28 (at 100 nM miR-26a).

C4b) Specificity.

We demonstrate that in ITP hybridization, MBs bind specifically to the correct target sequence. Molecular beacons have intrinsically high specificity, we here confirm that ITP conditions do not alter this property; and we experimentally verify that the detection of the miRNA target is not biased by the presence of other miRNA. To this end, we perform ITP hybridization on a mature miRNA whose sequence does not match the MB probe. We used the MB designed for detection of miR-26a and varied the concentration of a "model" exogenous miRNA in the TE: the mature miRNA sequence miR-126. The resulting titration curve is shown in FIG. 11 ("+" symbols). Together with the titration using the correct target (circles), we show titration with the incorrect miRNA sequence miR-126 as a control for hybridization specificity. The miR-126 control shows no increase in fluorescence, demonstrating the specificity of ITP hybridization.

C4c) Selectivity.

We now demonstrate the selectivity (associated here with molecule length) for miRNA of the ITP hybridization assay. Mature miRNAs are generated from processing of longer precursors, successively the pri-miRNA and pre-miRNA. The latter is about 70 nt long and is the shortest precursor preceding full miRNA maturation. Because these precursors contain the mature sequence, hybridization must be carried out exclusively on isolated, shorter miRNA, as in northern blotting. We achieve this by leveraging the variation of electrophoretic mobility of RNA with length. In a polymer sieving matrix, mobility decreases with increasing polynucleotide length. miRNA is the shortest class of RNA, hence its mobility is the greatest among all RNA. In particular it is greater than its precursors'. Therefore, careful selection of the trailing ion and polymer concentration allow for selective focusing of miRNA, excluding (longer) non-miRNA containing identical sequence.

To achieve high selectivity, we first chose an initial trailing ion (here MOPS) and selected a polymer concentration in LE2 that shows focusing of miRNA and MB (separately and simultaneously). We then adjusted LE2 polymer concentration (by increasing from the initial concentration) to reject pre-miRNA from the focused zone while retaining ITP focusing of miRNA and MBs. We found that 3% w/v PVP in LE2 matched this requirement. For the current conditions, we estimate our cut-off length to be about 60 nt (we focus only shorter RNA).

We also use FIG. 11 to illustrate the selectivity of this chemistry by comparing the aforementioned results for the short, mature miR-26a (here the capital "R" indicates a mature sequence, vs. the small case "r" which indicates a precursor) to results of focusing a sample of its 77 nt long precursor mir-26a ("x" symbols in FIG. 11). The enhancement f for the longer molecule sample mir-26a is globally much smaller than the signal generated by the mature miRNA. f remains at background level equivalent to about 1 nM mir-26a. We note a slight increase of fluorescence enhancement with increasing precursor concentration above 10 nM. We attribute this residual signal to hybridization of byproducts (present at low concentrations) resulting from imperfect RNA synthesis and PAGE purification (purity ~90% according to the manufacturer). These byproducts include short RNA fragments containing segments of the mature sequence, which can hybridize with MB.

Altogether, the data show fluorescence in the focused ITP zone is unaffected by non-target miRNA, and that MB signal is specific to miR-26a. The length selectivity and sequence specificity of our assay shows its efficacy to precisely detect specific miRNA sequences in total RNA samples.

C4d) miR-122 Profiling in Human Liver with ITP Hybridization.

To show the efficacy of the ITP hybridization assay in a biologically relevant case, we performed detection of miR-122 in two human tissue total RNA samples. We chose the following liver-specific miRNA target for its large dynamic range of expression: miR-122 is highly expressed in liver but poorly expressed in other organs. We diluted total RNA from human liver and kidney in TE down to 10 ng·$\mu L^{-1}$. We then performed the ITP hybridization assay on these samples with 100 pM MBs in the LE targeting miR-122.

Figure 12A:
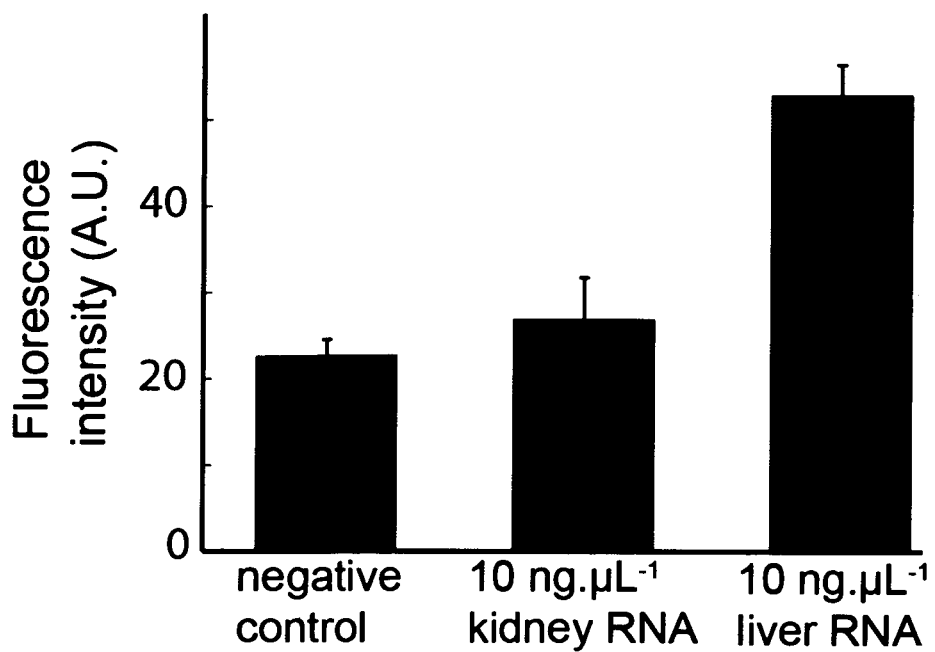
FIGS. 12a-b show ITP hybridization assay results for detection and quantification of miR-122 in kidney and liver.
Figure 12B:
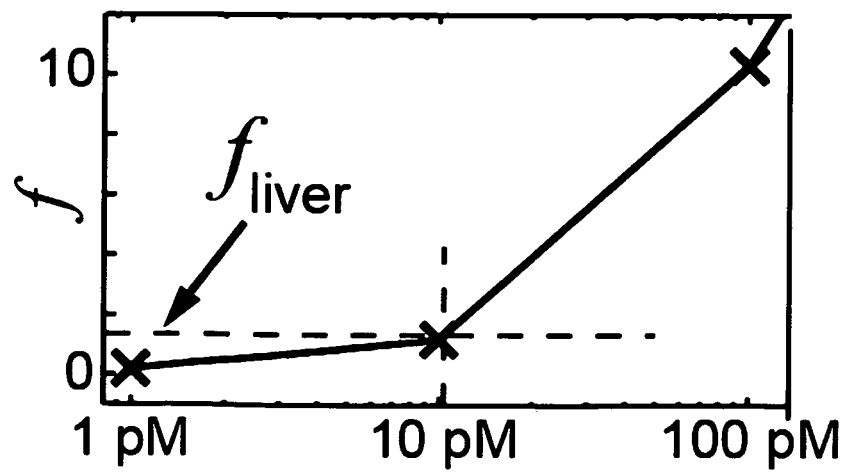

We show results of these experiments along with a negative control (blank run) in FIGS. 12a-b. These figures show a demonstration of ITP hybridization assay for detection and quantification of miR-122 in kidney and liver. We plot peak areas of ITP hybridization experiments where LEs initially contain 100 pM MBs targeting miR-122. The experiments shown have TEs which contain: a blank (FIG. 12a left bar), 10 ng·$\mu L^{-1}$ of total RNA from human kidney (FIG. 12a middle bar), and 10 ng·$\mu L^{-1}$ of total RNA from human liver (FIG. 12a right bar). The increase in fluorescence for kidney over the control is not statistically significant, showing our assay predicts miR-122 concentration in kidney below a limit of detection of 3,000 copies per cell. The peak area for liver is significantly greater, indicating greater expression of miR-122. We use a calibration curve built using synthetic miR-122 to estimate target concentration from fluorescence enhancement. The solid line on FIG. 12b shows a calibration curve resulting from interpolation of hybridization results from synthetic miR-122 versus concentration ("X" symbols). We use this curve to calculate the concentration corresponding to the enhancement $f_{liver}=1.3$. We estimate this concentration to be 10.3 pM, corresponding to approximately 16,000±400 copies per cell. Uncertainty bars represent 95% confidence on the mean.

ITP hybridization of miR-122 in kidney shows a slight increase in fluorescence (f=0.2), which is not statistically significant compared to negative control (failed the t-test). We conclude that the concentration of miR-122 in kidney is below the limit of detection of our assay. We estimate this limit to be 2 pM (f>0.4, see calibration below), which corresponds to 3,000 copies per cell (assuming 25 pg of RNA per cell). This is consistent with the amount of miR-122 measured in mouse kidney by RNase protection assay. Conversely, ITP hybridization of miR-122 in liver yields significant signal enhancement (f=1.3±0.15). This indicates that miR-122 is largely expressed in liver compared to kidney, confirming previous reports.

We performed quantification of miR-122 in liver using this measurement and leveraging a calibration curve we built with synthetic miR-122, in the same manner as the calibration of FIG. 11. We measured peak area of ITP hybridization of synthetic oligos dissolved at 1, 10 and 100 pM in the TE. We then perform a linear interpolation between the respective f values to yield a simple relation between fluorescence enhancement and miRNA concentration. We show a portion of this interpolation in FIG. 12b (solid line) for concentration values neighboring 10 pM. Using this calibration and the value of f found for liver ($f_{liver}$ in FIG. 12b), we calculated that a liver cell contains 16,000±400 copies of miR-122. This is on the same order of magnitude as an RNase protection assay (50,000 copies per cell) or RT-PCR measurements (10,000 copies per 10 pg of RNA or 25,000 copies per cell given our assumption on RNA mass per cell).

C5) Conclusion

We presented, characterized, and demonstrated an assay for the detection and quantification of miRNA targets in total RNA samples. The assay is based on an ITP process which selectively focuses miRNA and MB into an order 10 pL zone, in which we perform and analyze MB hybridization. We showed that ITP hybridization enables length-selective detection of miRNA and can distinguish miRNA from its precursors. We also showed that the sequence specificity of MBs was unaffected by coupling hybridization with ITP. Finally, we demonstrated the efficacy of the assay for the detection of miRNA targets in total RNA. We successfully detected miR-122 in liver and corroborated reduced expression in kidney. Using calibration experiments, we calculated the amount of miR-122 in liver; and our estimate is in fair agreement with measurements performed with other quantification methods. ITP hybridization is a fast (<2 min), low component cost (~$50 per chip, standard epifluorescence microscope and power supply, ~$0.50 of reagents per 100 runs), and sensitive (down to 3,000 copies per cell) microfluidic method for miRNA profiling that requires small amounts of sample (100 ng of total RNA) with about three decade dynamic range. Its speed, automation and low sample consumption make it an attractive alternative to PCR or northern blot analysis. We hypothesize that further optimization of ITP and MB chemistries and dynamics could significantly enhance sensitivity and reach the 100 copies per cell level. We also hypothesize that ITP hybridization can be extended to the detection and quantification of any type of nucleic acids, for example messenger, ribosomal RNA or genomic DNA.

The invention claimed is:
1. A method for sample analysis and/or preparation, the method comprising:
performing isotachophoresis (ITP) on a sample including at least one target species, wherein the target species is localized to a first ITP focus zone by the isotachophoresis;
providing at least one ligand to the isotachophoresis such that the ligand is localized to the first ITP focus zone by the isotachophoresis, wherein the target species and ligand bind to each other in the first ITP focus zone to form a bound complex;
wherein the ligand and/or the target comprises a nucleotide sequence; and
performing analysis of the bound complex to provide information on the target species.
2. The method of claim 1, wherein the ligand comprises at least one molecular beacon molecule having a fluorescence signal that increases substantially upon hybridization.
3. The method of claim 2, wherein the molecular beacon has a first end comprising a fluorophore and a second end comprising a quencher, wherein the first end is in sufficient proximity to the second end when the molecular beacon is not hybridized for the quencher to substantially suppress fluorescence from the fluorophore, and wherein the first end is sufficiently far from the second end when the molecular beacon is hybridized for fluorescence from the fluorophore to be substantially unaffected by the quencher.
4. The method of claim 1, wherein an effective mobility of the ligand and an effective mobility of the bound complex differ.
5. The method of claim 4, wherein the bound complex remains in the first ITP focus zone.
6. The method of claim 4, wherein the bound complex focuses in a second ITP focus zone distinct from the first ITP focus zone.
7. The method of claim 4, wherein the bound complex is not focused by the isotachophoresis.
8. The method of claim 4, further comprising separating the ligand, the target and/or the bound complex after formation of the bound complex.
9. The method of claim 8, wherein the separating the ligand, the target and/or the bound complex after formation of the bound complex comprises one or more methods selected from the group consisting of: isotachophoresis, electrophoresis, and chromatography.
10. The method of claim 1, wherein the at least one ligand provides a cooperative labeling of target species that bind two or more ligand molecules.
11. The method of claim 10, wherein the cooperative labeling is based on Förster resonance energy transfer (FRET), wherein a first bound probe molecule and a second bound probe molecule are adjacent to each other along the target species within the bound complex, wherein the first bound probe molecule includes a first fluorophore in proximity to the second bound probe molecule, wherein the second bound probe molecule includes a second fluorophore in proximity to the first bound probe molecule, and wherein excitation of the first fluorophore leads to emission from the second fluorophore by FRET.
12. The method of claim 1, wherein the sample further includes at least one precursor species of the at least one target species, and wherein the precursor species is not focused in the first ITP focus zone of the target species.
13. The method of claim 12, wherein the precursor species is also capable of binding to the ligands, whereby signals from the target species and the precursor species are spatially separated.
14. The method of claim 1, wherein the ligand is labeled with a fluorescent label.
15. The method of claim 1, wherein the target species is labeled with a fluorescent label, and wherein the ligand includes a quencher for the fluorescent label.
16. The method of claim 1, wherein the ligand comprises at least one nucleotide hybridization probe which is fluorescently labeled.
17. The method of claim 16, wherein the at least one target species is selected from the group consisting of: nucleic acid species, peptides capable of binding to a nucleic acid, polypeptides capable of binding to a nucleic acid, and proteins capable of binding to a nucleic acid.
18. The method of claim 16, wherein the at least one nucleotide hybridization probe is selected from the group consisting of: nucleic acid probes and aptamers.
19. The method of claim 1, further comprising partially hybridizing the target species and ligand prior to performing the isotachophoresis.
20. The method of claim 1, further comprising extracting bound complex from the first ITP focus zone.
21. The method of claim 1, wherein the analysis of the bound complex is performed in the first ITP focus zone.
22. A method for clinically screening for disease, the method comprising:

obtaining a patient specimen;
performing the method of claim 1, wherein the sample is derived from the patient specimen, and wherein the ligand is capable of binding to a target species that is a marker for disease.

\* \* \* \* \*